(12) United States Patent
Allan et al.

(10) Patent No.: US 10,779,874 B2
(45) Date of Patent: Sep. 22, 2020

(54) METHODS AND SYSTEMS FOR TREATING URINARY STRESS INCONTINENCE

(71) Applicant: Viveve, Inc., Sunnyvale, CA (US)

(72) Inventors: Bruce Baldwin Allan, Calgary (CA); Deborah Suzanne Wilkerson, Collierville, TN (US); David Laurence Black, Cameron, MT (US); Perry Joseph Tomasetti, Pepperell, MA (US)

(73) Assignee: VIVEVE, INC., Sunnyvale, CA (US)

( * ) Notice: Subject to any disclaimer, the term of this patent is extended or adjusted under 35 U.S.C. 154(b) by 710 days.

(21) Appl. No.: 15/268,398

(22) Filed: Sep. 16, 2016

(65) Prior Publication Data

US 2017/0071651 A1    Mar. 16, 2017

Related U.S. Application Data

(60) Provisional application No. 62/219,354, filed on Sep. 16, 2015.

(51) Int. Cl.
*A61B 18/04* (2006.01)
*A61B 18/02* (2006.01)
(Continued)

(52) U.S. Cl.
CPC .............. *A61B 18/04* (2013.01); *A61B 18/02* (2013.01); *A61B 18/12* (2013.01);
(Continued)

(58) Field of Classification Search
CPC ......... A61B 18/02; A61B 18/04; A61B 18/12; A61B 18/20; A61B 18/1485;
(Continued)

(56) References Cited

U.S. PATENT DOCUMENTS

| 5,143,063 A | 9/1992 | Fellner |
| 5,755,753 A | 5/1998 | Knowlton |

(Continued)

FOREIGN PATENT DOCUMENTS

WO    2014165242 A1    10/2014

OTHER PUBLICATIONS

International Search Report and Written Opinion in International Application No. PCT/US2016/052320, dated Dec. 20, 2016.

(Continued)

*Primary Examiner* — Eun Hwa Kim
*Assistant Examiner* — Catherine Premraj
(74) *Attorney, Agent, or Firm* — Venable LLP; Michele V. Frank

(57) ABSTRACT

The systems and methods in accordance with the principles of the invention can treat urinary stress incontinence by treating target tissue in proximity to the urethra and/or bladder neck. A method for treating urinary stress incontinence in a subject can included non-invasively heating a subsurface region of a target tissue to induce remodeling of the subsurface region at the anterior and/or posterior regions of the vagina. The system can include: a controller and a probe having a distal end configured for non-invasive contact with a surface of a target tissue to transfer energy to the target tissue based on treatment parameters. The probe distal end can have two treatment surfaces spaced apart a distance equal to at least a width of a urethra.

38 Claims, 11 Drawing Sheets

(51) Int. Cl.
*A61B 18/12* (2006.01)
*A61N 7/02* (2006.01)
*A61B 18/18* (2006.01)
*A61B 18/20* (2006.01)
*A61B 18/14* (2006.01)
*A61B 18/00* (2006.01)

(52) U.S. Cl.
CPC ...... *A61B 18/1485* (2013.01); *A61B 18/1815* (2013.01); *A61B 18/20* (2013.01); *A61N 7/02* (2013.01); *A61B 2018/00005* (2013.01); *A61B 2018/00523* (2013.01); *A61B 2018/00559* (2013.01); *A61B 2018/00589* (2013.01)

(58) Field of Classification Search
CPC ...... A61B 18/1815; A61B 2018/00005; A61B 2018/00523; A61B 2018/00559; A61B 2018/00589; A61N 7/02
See application file for complete search history.

(56) References Cited

U.S. PATENT DOCUMENTS

| | | | |
|---|---|---|---|
| 5,919,219 | A | 7/1999 | Knowlton |
| 6,350,276 | B1 | 2/2002 | Knowlton |
| 6,387,380 | B1 | 5/2002 | Knowlton |
| 6,425,912 | B1 | 7/2002 | Knowlton |
| 6,453,202 | B1 | 9/2002 | Knowlton |
| 6,463,331 | B1 | 10/2002 | Edwards |
| 6,607,525 | B2 | 8/2003 | Franco |
| 6,751,507 | B2 | 6/2004 | Morrison et al. |
| 6,840,954 | B2 | 1/2005 | Dietz et al. |
| 7,315,762 | B2 | 1/2008 | Mosher et al. |
| 7,792,589 | B2 | 9/2010 | Levy, Jr. et al. |
| 7,837,682 | B2 | 11/2010 | Ostrovsky et al. |
| 8,709,057 | B2 | 4/2014 | Tettamanti et al. |
| 8,961,511 | B2 | 2/2015 | Parmer |
| 2002/0049483 | A1 | 4/2002 | Knowlton |
| 2003/0212393 | A1* | 11/2003 | Knowlton ............ A45D 44/22 606/32 |
| 2003/0236487 | A1 | 12/2003 | Knowlton |
| 2004/0000316 | A1 | 1/2004 | Knowlton et al. |
| 2005/0154433 | A1† | 7/2005 | Levy |
| 2005/0288680 | A1* | 12/2005 | Ingle ................ A61B 18/1482 606/99 |
| 2006/0224090 | A1 | 10/2006 | Ostrovsky et al. |
| 2006/0241530 | A1 | 10/2006 | Ostrovsky et al. |
| 2007/0219602 | A1 | 9/2007 | Ostrovsky et al. |
| 2011/0004205 | A1 | 1/2011 | Chu et al. |
| 2011/0178584 | A1* | 7/2011 | Parmer ................ A61B 90/06 607/102 |
| 2012/0136407 | A1 | 5/2012 | Presthus et al. |
| 2014/0324036 | A1 | 10/2014 | Sachs et al. |
| 2015/0165241 | A1* | 6/2015 | Burdette ................ A61B 8/12 601/3 |
| 2015/0202467 | A1 | 7/2015 | Diederich et al. |
| 2015/0297908 | A1* | 10/2015 | Alinsod ................ A61N 1/403 607/102 |

OTHER PUBLICATIONS

Macrene Alexiades, MD, PhD., et al., "Randomized, Blinded, 3-Arm Clinical Trial Assessing Optimal Temperature and Duration for Treatment With Minimally Invasive Fractional Radiofrequency", American Society for Dermatoligic Surgery, 2015, 41:623-632 (10 pages).

Dany Berube, PhD., et al., "A Predictive Model of Minimally Invasive Bipolar Fractional Radiofrequency Skin Treatment", Lasers in Surgery and Medicine, 2009, 41:473-478 (6 pages).

Femilift | Alma Surgical "Clinical Solutions for a Better Feminine Life", retrieved Sep. 16, 2015 from http://www.almasurgical.com/applications/femililift/ (8 pages).

IncontiLase | Gynecology | Fotona, retrieved Sep. 16, 2015 from http://www.fotona.com/en/treatments/1309/incontilase/ (3 pages).

Venn Healthcare "Petite Lady", retrieved Sep. 16, 2015 from http://vennhealthcare.com/petite-lady (4 pages).

* cited by examiner
† cited by third party

METHODS AND SYSTEMS FOR TREATING URINARY STRESS INCONTINENCE

CROSS-REFERENCE OF RELATED APPLICATION

This application claims priority to U.S. Provisional Application No. 62/219,354 filed Sep. 16, 2015; the entire contents of all of which are hereby incorporated by reference.

BACKGROUND

1. Technical Field

The field of the currently claimed embodiments of this invention relates to a method and apparatus for treating urinary stress incontinence, such as by the application of radiant energy.

2. Discussion of Related Art

Urinary incontinence is a socially disabling condition that affects millions of women of all ages and ethnicities. Urinary stress incontinence is defined by the involuntary loss of urine during increased intra-abdominal pressure in the absence of a detrusor contraction. Increased intra-abdominal pressure can be caused by coughing, sneezing, laughing, exercising, and lifting heavy objects, for example. Urinary stress incontinence is the most common type of female urinary incontinence, affecting more than an estimated 7 million women in the United States. Current methods of treatment of urinary stress incontinence are typically invasive. Accordingly, there is a need for a non-invasive, non-pharmaceutical treatment for urinary stress incontinence in women.

SUMMARY

An embodiment of the invention relates to a system for treating urinary stress incontinence in a subject. The system includes: a controller coupled to a probe to treat urinary stress incontinence, the probe having a distal end configured for non-invasive contact with a surface of a target tissue and having a proximal end coupled to the controller; and at least one urinary stress incontinence treatment parameter. The at least one urinary stress incontinence treatment parameter is selected to achieve a predetermined temperature for a predetermined time period in a target tissue to induce remodeling of the target tissue to treat urinary stress incontinence. The controller coupled to the probe is configured to transfer energy to the target tissue based on the at least one urinary stress incontinence treatment parameter to produce at least one of heat and cooling in a subsurface region of the target tissue to the predetermined temperature for the predetermined time period to induce remodeling of the subsurface region to treat urinary stress incontinence.

An embodiment of the invention relates to the system described above, where the at least one urinary stress incontinence treatment parameter includes an anterior vaginal energy output parameter to achieve an anterior vaginal predetermined temperature for a predetermined time in the target tissue to induce remodeling of the subsurface region of an anterior vaginal wall to treat urinary stress incontinence, and the anterior vaginal energy output parameter is configured as an energy transfer sequence including energy pulse duration, energy pulse timing, and energy pulse coordinates on the anterior vaginal wall to induce remodeling of the subsurface region to treat urinary stress incontinence.

An embodiment of the invention relates to the system described above, where the at least one urinary stress incontinence treatment parameter includes a posterior vaginal energy output parameter to achieve a posterior vaginal predetermined temperature for a predetermined time in the target tissue to induce remodeling of the subsurface region of a posterior vaginal wall to treat urinary stress incontinence, and the posterior vaginal energy output parameter is configured as another energy transfer sequence including energy pulse duration, energy pulse timing, and energy pulse coordinates on the posterior vaginal wall to induce remodeling of the subsurface region to treat urinary stress incontinence.

An embodiment of the invention relates to the system described above, where the distal end of the probe includes a treatment surface configured for non-invasive contact with the surface of the target tissue, the treatment surface has a width between 1 cm and 3 cm, and a length between 4 cm and 6 cm.

An embodiment of the invention relates to the system described above, where the distal end of the probe includes a first treatment surface and a second treatment surface spaced apart from the first treatment surface, wherein the first and second treatment surfaces are spaced apart a distance equal to at least a width of a urethra.

An embodiment of the invention relates to a method for treating urinary stress incontinence in a subject. The method includes the steps of: non-invasively heating a subsurface region of a target tissue to a temperature for a period of time sufficient to induce a remodeling of the subsurface region; and inducing remodeling of the subsurface region to treat urinary stress incontinence.

An embodiment of the invention relates to a method for treating urinary stress incontinence in a subject as described above, where the step of inducing remodeling of the subsurface region further includes inducing positioning of a urethra to treat urinary stress incontinence.

An embodiment of the invention relates to a method for treating urinary stress incontinence in a subject as described above, where the step of non-invasively heating further includes heating to at least one of a predetermined temperature for a predetermined period of time to induce remodeling of the subsurface region to treat urinary incontinence.

An embodiment of the invention relates to a method for treating urinary stress incontinence in a subject as described above, where the step of non-invasively heating further includes heating an anterior vaginal wall proximate and apart from a urethra of the subject, and avoiding directly heating the urethra to the temperature, and inducing remodeling of the subsurface region to create a buttress of remodeled tissue to support the urethra to treat urinary stress incontinence.

An embodiment of the invention relates to a method for treating urinary stress incontinence in a subject as described above, where the step of non-invasively heating includes heating an anterior vaginal wall proximate and apart from a urethra of the subject and heating a posterior vaginal wall substantially diametrically opposed to the heated anterior vaginal wall, the sidewalls between the anterior and posterior vaginal walls remain untreated with heat.

An embodiment of the invention relates to a method for treating urinary stress incontinence in a subject as described above, where the step of non-invasively heating further includes heating a posterior vaginal wall, inducing remodeling of the subsurface region of the posterior vaginal wall to treat urinary stress incontinence by the remodeled vaginal wall providing a buttress of remodeled tissue to support an anterior vaginal wall when compressed against the posterior vaginal wall.

An embodiment of the invention relates to a method for treating urinary stress incontinence in a subject as described above, where the method further includes the step of cooling the target tissue.

An embodiment of the invention relates to a method for treating urinary stress incontinence in a subject as described above, where the step of non-invasively heating includes: heating at least part of a first portion of a vagina of the subject, the first portion located on an anterior vaginal wall extending from about 0.25 cm to a left of a urethra of the subject to about 2 cm to the left of the urethra; and heating at least part of a second portion of the vagina, the second portion located on the anterior vaginal wall extending from about 0.25 cm to the right of the urethra to about 2 cm to the right of the urethra. The non-invasively heating includes heating a portion of the vagina extending from a hymen inwardly to a location from 4.0 cm to 6.0 cm from the hymen.

An embodiment of the invention relates to a method for treating urinary stress incontinence in a subject as described above, where the step of non-invasively heating the target tissue further includes heating at least part of a third portion of the vagina. The third portion is located on a posterior vaginal wall extending from about 3.0 cm to a left of a midline to about 3.0 cm to a right of the midline.

An embodiment of the invention relates to a method for treating urinary stress incontinence in a subject as described above, where any tissue residing outside of the first portion, the second portion or the third portion is not treated.

An embodiment of the invention relates to a method for treating urinary stress incontinence in a subject as described above, where the step of non-invasively heating includes heating the target tissue to a temperature between 45 degrees C. and 65 degrees C.

An embodiment of the invention relates to a method for treating urinary stress incontinence in a subject as described above, where the step of non-invasively heating includes heating the target tissue to a temperature between 54 degrees C. and 60 degrees C.

An embodiment of the invention relates to a method for treating urinary stress incontinence in a subject as described above, where the step of non-invasively heating further includes delivering of at least one of radiofrequency energy, microwave energy, laser energy, or ultrasound energy.

An embodiment of the invention relates to a method for treating urinary stress incontinence in a subject as described above, where the period of time sufficient to induce remodeling of the subsurface region is between 1 second to 5 seconds.

An embodiment of the invention relates to a method for treating urinary stress incontinence in a subject as described above, where the period of time sufficient to induce remodeling of the subsurface region is between 2 seconds to 4 seconds.

An embodiment of the invention relates to a method for treating urinary stress incontinence in a subject as described above, where the step of non-invasively heating further includes heating a submucosa tissue layer.

An embodiment of the invention relates to a method for treating urinary stress incontinence in a subject as described above, where a step of cooling a surface region of the target tissue is included.

An embodiment of the invention relates to a method for treating urinary stress incontinence in a subject as described above, where the cooling of the surface region of the target tissue includes contacting an epithelial tissue layer of the target tissue with a treatment tip, the treatment tip including a cooling mechanism.

An embodiment of the invention relates to a method for treating urinary stress incontinence in a subject as described above, where the cooling of the surface region includes cooling the epithelial tissue layer to a temperature between 0 degrees C. and 10 degrees C.

An embodiment of the invention relates to a method for treating urinary stress incontinence in a subject as described above, where a step of contacting an epithelial tissue layer of a vagina of the subject with a treatment tip at two or more contact sites during a procedure is included. The treatment tip includes an energy delivery element adapted to non-invasively heat the target tissue.

An embodiment of the invention relates to a method for treating urinary stress incontinence in a subject as described above, where the step of contacting an epithelial tissue layer of the vagina with a treatment tip at two or more contact sites is repeated at least twice during the procedure such that each of the two or more contact sites is contacted at least twice.

An embodiment of the invention relates to a method for treating urinary stress incontinence in a subject as described above, where the step of contacting an epithelial tissue layer of the vagina with a treatment tip at two or more contact sites is repeated at least five times during the procedure such that each of the two or more contact sites is contacted at least five times.

An embodiment of the invention relates to a method for treating urinary stress incontinence in a subject as described above, where the remodeling includes at least one of contracting target tissue, denaturing collagen, tightening collagen-rich sites in the target tissue, or releasing heat shock proteins.

An embodiment of the invention relates to a method for treating urinary stress incontinence in a subject as described above, where at least some of the remodeling occurs during the step of non-invasively heating.

An embodiment of the invention relates to a method for treating urinary stress incontinence in a subject as described above, where including cooling a surface region of the target tissue for a first period of time; and cooling the surface region of the target tissue for a second period of time. The first period of time is shorter than the second period of time. The step of non-invasively heating includes delivering energy by contacting an epithelial tissue layer in a vagina of the subject with a treatment tip, the treatment tip including an energy delivery element. The step of non-invasively heating includes heating a portion in the vagina extending from a hymen inwardly to a location from 4.0 cm to 6.0 cm from the hymen.

An embodiment of the invention relates to a method for treating urinary stress incontinence in a subject as described above, where the step of non-invasively heating further includes heating a submucosa tissue layer. The step of cooling of the surface region of the target tissue for a first period of time further includes cooling an epithelial tissue layer, and the step of cooling of the surface region of the target tissue for a second period of time further includes cooling the epithelial tissue layer.

An embodiment of the invention relates to a method for treating urinary stress incontinence in a subject as described above, where the step of cooling of the surface region of the target tissue for a first period of time and the step of cooling of the surface region of the target tissue for a second period of time each further include contacting an epithelial tissue layer with a treatment tip, the treatment tip including a cooling mechanism.

An embodiment of the invention relates to a method for treating urinary stress incontinence in a subject as described above, where the step of cooling of the surface region of the target tissue for a first period of time and the step of cooling of the surface region of the target tissue for a second period of time each further include cooling the surface region of the target tissue to a temperature between 0 degrees C. and 10 degrees C.

An embodiment of the invention relates to a method for treating urinary stress incontinence in a subject as described above, where the step of non-invasively heating includes heating at least part of a first portion of a vagina of the subject circumferentially around a wall of the vagina from 11 o'clock to 1 o'clock. An aspect closest to a urethra of the subject is 12 o'clock.

An embodiment of the invention relates to a method for treating urinary stress incontinence in a subject as described above, where the step of non-invasively heating further includes heating a portion of the vagina extending from a hymen inwardly to a location from 4.0 cm to 6.0 cm from the hymen.

An embodiment of the invention relates to a method for treating urinary stress incontinence in a subject as described above, where the step of non-invasively heating further includes heating at least part of a second portion of the subject's vagina circumferentially around a wall of the subject's vagina between 5 o'clock to 7 o'clock, and the second portion is diametrically opposed to the first portion.

An embodiment of the invention relates to a method for treating urinary stress incontinence in a subject as described above, where any tissue residing outside of the first portion or the second portion is not treated.

An embodiment of the invention relates to a method for treating urinary stress incontinence in a subject as described above, where the step of non-invasively heating includes one of: heating the target tissue to a temperature between 45 degrees C. and 65 degrees C.; and heating the target tissue to a temperature between 54 degrees C. and 60 degrees C.

An embodiment of the invention relates to a method for treating urinary stress incontinence in a subject as described above, where the period of time sufficient to induce remodeling of the target tissue is one of between 1 second to 5 seconds and between 2 seconds to 4 seconds.

An embodiment of the invention relates to a method for treating urinary stress incontinence in a subject as described above, where the method includes a step for cooling a surface region of the target tissue. The cooling of the surface region of the target tissue includes contacting an epithelial tissue layer of the target tissue with a treatment tip, the treatment tip including a cooling mechanism.

An embodiment of the invention relates to a method for treating urinary stress incontinence in a subject as described above, where the method includes cooling the surface region of the target tissue by cooling the epithelial tissue layer to a temperature between 0 degrees C. and 10 degrees C.

An embodiment of the invention relates to a method for treating urinary stress incontinence in a subject as described above, where the step of non-invasively heating includes at least one of heating at least part of a second portion of the vagina circumferentially around a wall of the vagina between 1 o'clock to 5 o'clock and heating at least part of a second portion of the vagina circumferentially around a wall of the vagina between 7 o'clock to 11 o'clock.

According to some embodiments of the invention, a probe for treating urinary stress incontinence includes a treatment tip configured for non-invasive contact with a surface of a target tissue. The treatment tip includes a first epithelium-contacting treatment surface comprising a first energy-delivery element, and a second epithelium-contacting treatment surface spaced apart from the first treatment surface. The second epithelium-contacting treatment surface includes a second energy delivery element. The probe further includes a controller in communication with the first energy-delivery element and the second energy-delivery element. The second treatment surface is spaced apart from the first treatment surface by a distance equal to at least a width of a urethra of a patient being treated. The controller is configured to control the first and second energy-delivery elements to heat or cool at least a portion of the first and second epithelium-contacting treatment surfaces to induce remodeling of the target tissue to treat urinary stress incontinence.

According to some embodiments of the invention, the controller is configured to control the first and second energy-delivery elements to heat or cool a first portion of the first and second epithelium-contacting treatment surfaces while simultaneously heating or cooling a second portion of the first and second epithelium-contacting treatment surfaces. According to some embodiments, the distance equal to at least a width of a urethra of a patient being treated is between 0.25 cm and 1 cm. According to some embodiments, at least one of the treatment surfaces has a length of between 2 cm and 6 cm and a width of between 0.5 cm to 2 cm. According to some embodiments, at least one of the treatment surfaces has a length of between 2 cm and 6 cm and a width of between 0.5 cm to 2 cm. According to some embodiments, the probe further includes a position adjust mechanism for adjusting a distance between the first and second epithelium-contacting treatment surfaces.

BRIEF DESCRIPTION OF THE DRAWINGS

Further objectives and advantages will become apparent from a consideration of the description, drawings, and examples.

DETAILED DESCRIPTION

Figure 1:
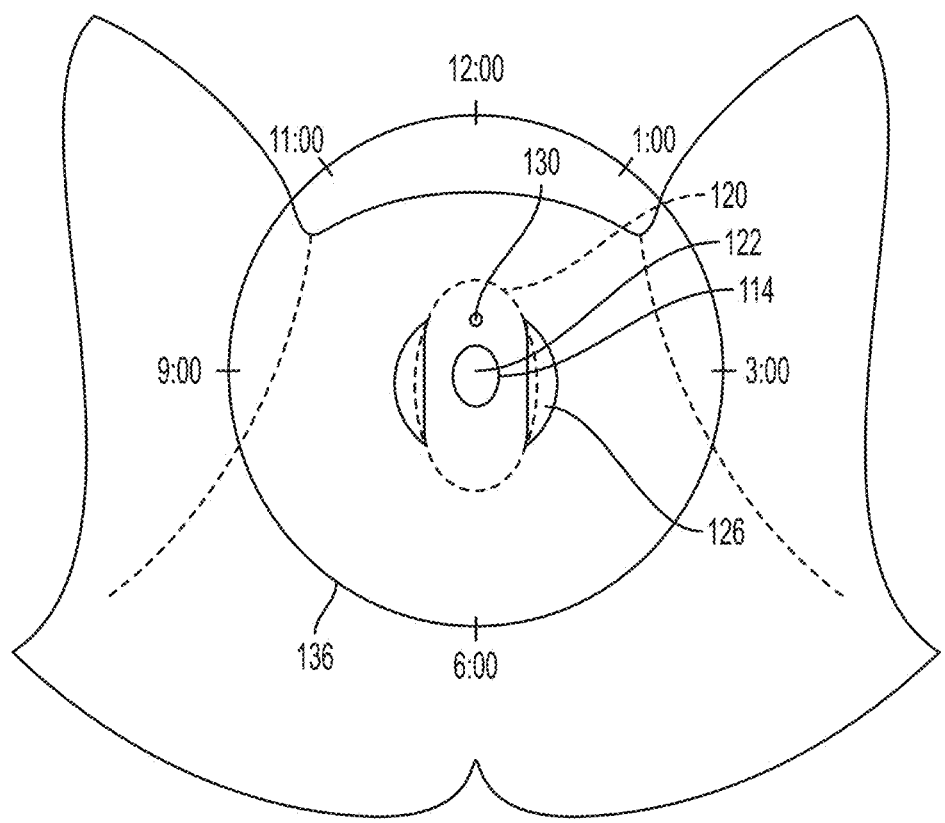
FIG. 1 is a schematic view of female genitalia, as well as an orienting clock to provide a circumferential reference scheme for the vaginal wall.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Radiofrequency treatment can be applied on a microscopic level to perform microremodeling such that radiofrequency energy is used to denature collagen without significant necrosis or injury to vascular or nerve tissues. The application of radiofrequency energy for urinary stress incontinence can include the laparoscopic approach, the transvaginal approach, and the transurethral approach. The laparoscopic approach uses laparoscopy to enter the space of Retzius, and the tip of an electrothermal applicator is inserted lateral to the urethra. Treatment is carried out on both sides of the urethra until all of the exposed endopelvic fascia is treated. The transvaginal approach entails hydrodissection of the anterior vaginal wall, after which a 2- to 3-cm incision is made 1 cm lateral to the urethra. On the lateral border, dissection of the anterior vaginal wall is performed to expose the inferior portion of the endopelvic fascia. This is carried out on both sides of the urethra. The tip of a radiofrequency energy applicator is applied to the underlying endopelvic fascia with enough pressure to cause deflection of the tissue, and is drawn in along the longitudinal axis of the medial border in a slow, sweeping manner as the energy is applied. The transurethral approach requires the delivery of oral sedatives and local anesthesia to the patient prior to introducing a radiofrequency device through the urethra. The radiofrequency device includes a shaft and a balloon with four needle electrodes. The electrodes are deployed to penetrate the mucosa, positioning the needle tips within the submucosa and the superficial smooth muscle. Radiofrequency and irrigation are simultaneously delivered by the device, creating four lesions. Radiofrequency treatments have been used to tighten tissue of the female genitalia, see the assignee's patents U.S. Pat. Nos. 8,961,511 and 9,271,785, both of which are incorporated herein by reference in their entireties.

There remains a need for a non-invasive (i.e., non-surgical), non-pharmaceutical, reliable and effective treatment for urinary stress incontinence especially for females.

By utilizing the tissue in proximity to the urethra and bladder to buttress and/or support the urethra, bladder neck and/or bladder, the systems and methods described herein can treat urinary stress incontinence, as discussed in more detail throughout this application.

Access to this tissue can be made by way of the vaginal canal. By accessing through the vagina, the tissue in, around and between the vaginal canal and the urethra/bladder neck/bladder can be treated non-invasively and non-surgically. By treating specific areas, as discussed in more detail herein, anterior and posterior buttressing of the urethra can be achieved. One way this can be done is by non-invasively accessing the tissue through the vaginal canal and applying energy, in the form or heat and/or cooling, to the subsurface region of the target tissue to induce remodeling of the subsurface region to treat urinary stress incontinence. Various methods and systems are described herein to induce remodeling of target tissue to treat urinary stress incontinence.

An embodiment of the invention relates to a system for treating urinary stress incontinence in a subject. The system generally includes a treatment probe coupled to a controller. An exemplary system is disclosed in assignee's U.S. Pat. No. 9,271,785, which is incorporated herein by reference.

Figure 8A:
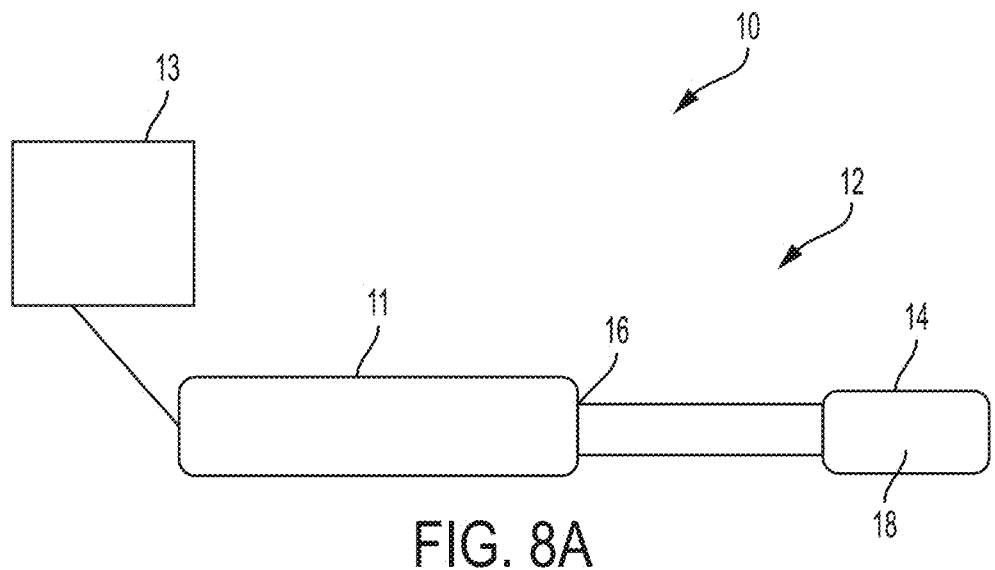
FIG. 8A illustrates an apparatus for applying energy to the target tissue.

Exemplary probes are shown in FIGS. 8A-8D, and modifications can be made in order to treat the target tissue effectively and efficiently. FIG. 8A shows an exemplary treatment device 10 for treating urinary stress incontinence in a subject. A probe is shown generally at reference numeral 12 to treat urinary stress incontinence. The probe 12 has a distal end 14 configured for non-invasive contact with a surface of a target tissue, and has a proximal end 11 coupled by an arm 16 to the distal end 14. Any exemplary probe construction is provided in assignee's U.S. Pat. No. 9,271,785, which is incorporated herein by reference. In accordance with the principles of the inventions herein, a controller 13 in communication with the probe controls the parameters for the treatment of the urinary stress incontinence. The at least one urinary stress incontinence treatment parameter is selected to achieve a predetermined temperature for a predetermined time period in a target tissue to induce remodeling of the target tissue to treat urinary stress incontinence. The controller coupled to the probe is configured to transfer energy to the target tissue based on the at least one urinary stress incontinence treatment parameter to produce at least one of heat and cooling in a subsurface region of the target tissue to the predetermined temperature for the predetermined time period to induce remodeling of the subsurface region to treat urinary stress incontinence. The distal end 14 of probe 12 has a treatment surface 18 for contacting the target tissue. In some embodiments, the controller 13 can be disposed within the proximal end 11 of the probe 12. In some embodiments, the proximal end 11 of the probe 12 may form a handle to allow a user to hold and manipulate the probe 12 during treatment.

As shown in FIG. 8A, the treatment surface 18 according to some embodiments comprises a single treatment surface. The treatment surface 18 may be flat, or may be curved or angled to achieve better contact with the curved surface of the vaginal wall. In some embodiments, the treatment surface, which comes into contact with surface regions of the target tissues, may have a total surface area of between 0.5 cm² and 36 cm². The total length of the treatment surface can be between about 1 cm and about 6 cm. The total width of the treatment surface according to some embodiments is between about 0.5 cm and about 6 cm. The total width of the treatment surface according to some embodiments is between about 0.5 cm and about 4 cm. The total width of the treatment surface according to some embodiments is between about 1 cm and about 2 cm. One of skill in the art may contemplate other lengths and widths that are appropriate for treating target tissue, and would understand the embodiments of the invention to include devices having these configurations. According to some embodiments, the treatment surface has a length that allows a user to apply treatment to a patient's vagina by solely moving the probe laterally within the vagina, and without changing the probe's depth in the vagina. For example, the treatment surface may have a length that is approximately equal to the depth of treatment into the vagina.

Figure 8B:
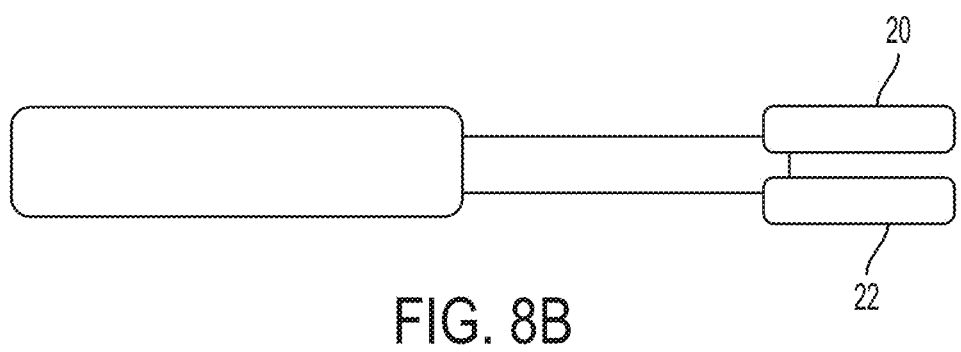
FIG. 8B illustrates another apparatus for applying energy to the target tissue where the treatment tip has separated treatment surfaces.
Figure 8C:
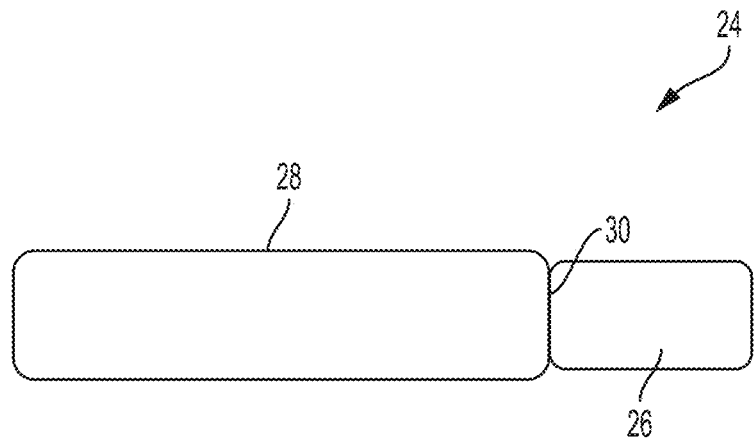
FIG. 8C is an illustration of an apparatus for applying energy to the target tissue, wherein the treatment surface extends to the proximal portion of the apparatus.

A probe 24 according to some embodiments is shown in FIG. 8C. The probe 24 includes a treatment surface 26 that extends all the way to the proximal portion 28 of the probe 24. The treatment surface 26 may be directly coupled to the proximal portion 28 at the proximal end 30 of the treatment surface 26, or may be joined to the proximal portion 28 by a connecting arm, as shown in FIG. 8A. The treatment surface 26 may have a total surface area between 0.5 cm² and 36 cm². The total length of the treatment surface can be between about 1 cm and about 6 cm. The total width of the treatment surface according to some embodiments is between about 0.5 cm and about 6 cm. The total width of the treatment surface according to some embodiments is between about 1 cm and about 4 cm. The total width of the treatment surface according to some embodiments is about 2 cm. One of skill in the art may contemplate other lengths and widths that are appropriate for treating target tissue, and would understand the embodiments of the invention to include devices having these dimensions.

FIG. 8B shows a probe having a distal end that is bifurcated, split, or separated to have spaced apart treatment surfaces or windows. By having two treatment surfaces spaced apart from each other, treatment can be applied to the anterior wall of a patient's vagina while avoiding the urethra. Various configurations are contemplated to enable treatment of the region around the urethra while avoiding the portion of the vagina directly above with the urethra, which runs along the center of the anterior wall of the vagina. In FIG. 8B, the treatment surface is configured to take the shape of two treatment surfaces 20, 22, which are spaced apart from one another. The two treatment surfaces can enable a user to treat both sides of the anterior wall of a patient's vagina without moving the probe, and without treating the portion of the vagina above the urethra.

The probe may further include and adjustment mechanism for drawing the treatment surfaces closer together, or for moving them farther apart. According to some embodiments, the adjustment mechanism can allow the treatment surfaces to be moved such that they are adjacent to one another and form a continuous treatment surface, like the treatment surface 18 in FIG. 8A. Such a configuration could be used, for example, to treat the posterior surface of the vagina, which can be treated as a continuous treatment area. The two treatment surfaces may be positioned parallel to one another. Alternatively, the treatment surfaces may be positioned at an angle with respect to one another and to the probe, such that they are better configured to make contact with the curved vaginal wall.

The treatment surfaces may include one or more energy-delivery elements. The energy delivery elements may enable heating or cooling of an entire treatment surface at once. Alternatively, each energy delivery element may enable heating or cooling of multiple portions of the treatment surface, individually or simultaneously. Each of the two treatment surfaces may also have a plurality of energy-delivery elements that can heat or cool sections of the treatment surface separately and/or in succession. For example, the treatment surface 20 may be divided into a number of sections along its length. Heating may be applied for a first period of time in the first section, and once the first period of time ends, heating of the first section may end, while heating of the second section may begin. This may continue along the length of the treatment tip, until all sections of the treatment surface 20 have undergone heating. The treatment surface 22 may undergo a similar heating process at the same time, or the processes may be conducted at different times. Multiple treatments can occur at one location.

Further, the treatment surfaces may be configured such that individual sections can undergo cooling. For example, the first section may undergo cooling prior to heating of the first section. The cooling may cease while the heating of the first section takes place. During this period, the second section may undergo a cooling process. When the heating of the first section ends, cooling of the first section may resume for a period of time, while heating of the next section begins. This process may continue along the length of the treatment surfaces. This process is purely exemplary, and other combinations and patterns of heating and cooling may also be used. The controller 13 may control the energy-delivery elements to achieve the desired treatment pattern.

According to some embodiments, the total surface area of the two treatment surfaces is between about 2 cm² and about 36 cm². The length of each of the two treatment surfaces is between about 1 cm and about 6 cm. The width of each of the two treatment surfaces according to some embodiments is between about 0.5 cm and about 3 cm. The width of each of the two treatment surfaces according to some embodiments is between about 0.5 cm and about 2 cm. The width of the area separating the two treatment surfaces is between about 0.5 cm and about 1 cm. In some embodiments, each treatment surface has a width of about 1 cm and a length of about 6 cm. The spaced-apart treatment surfaces can also be attached at the base and form a generally U-shape configuration, for example.

Figure 8D:
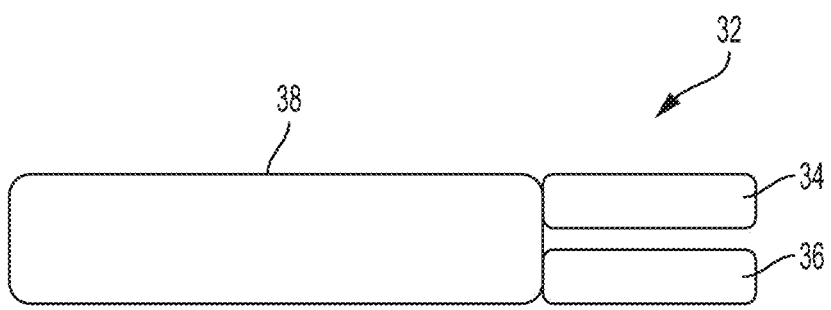
FIG. 8D is an illustration of an apparatus for applying energy to the target tissue, wherein the two treatment surfaces extend to the proximal portion of the apparatus.

A probe 32 according to some embodiments is shown in FIG. 8D. The probe 32 includes a first treatment surface 34 and a second treatment surface 36 that extend all the way to the proximal portion 38 of the probe 32. The treatment surfaces 34, 36 may be directly coupled to the proximal portion 38 at the proximal end of the treatment surfaces 34, 36, or may be joined to the proximal portion 38 by a connecting arm, as shown in FIG. 8B. The treatment surfaces 34, 36 may have a total surface area of between 1 cm² and 36 cm². The length of each of the treatment surfaces can be between about 1 cm and about 6 cm. The width of each of the treatment surfaces according to some embodiments is between about 0.5 cm and about 3 cm. The width of each of the treatment surfaces according to some embodiments is between about 0.5 cm and about 2 cm. The width of each of the treatment surfaces according to some embodiments is about 1 cm. One of skill in the art may contemplate other lengths and widths that are appropriate for treating target tissue, and would understand the embodiments of the invention to include devices having these configurations.

A system for treating urinary stress incontinence in a subject can include a controller coupled to a probe to treat urinary stress incontinence. As described above, the probe can have a distal end configured for non-invasive contact with a surface of a target tissue and a proximal end coupled to the controller. The system also includes at least one urinary stress incontinence treatment parameter. The urinary stress incontinence treatment parameter is selected to achieve a predetermined temperature for a predetermined time period in a target tissue to induce remodeling of the target tissue to treat urinary stress incontinence. The controller coupled to the probe is configured to transfer energy to the target tissue based on the at least one urinary stress incontinence treatment parameter to produce at least one of heat and cooling in a subsurface region of the target tissue to the predetermined temperature for the predetermined time period to induce remodeling of the subsurface region to treat urinary stress incontinence.

An embodiment of the invention relates to the system described above, where the at least one urinary stress incontinence treatment parameter includes an anterior vaginal energy output parameter to achieve an anterior vaginal predetermined temperature for a predetermined time in the target tissue to induce remodeling of the subsurface region of an anterior vaginal wall to treat urinary stress incontinence, and the anterior vaginal energy output parameter is configured as an energy transfer sequence including energy pulse duration, energy pulse timing, and energy pulse coordinates on the anterior vaginal wall to induce remodeling of the subsurface region to treat urinary stress incontinence.

An embodiment of the invention relates to the system described above, where the at least one urinary stress incontinence treatment parameter includes a posterior vaginal energy output parameter to achieve a posterior vaginal predetermined temperature for a predetermined time in the target tissue to induce remodeling of the subsurface region of a posterior vaginal wall to treat urinary stress incontinence, and the posterior vaginal energy output parameter is configured as another energy transfer sequence including energy pulse duration, energy pulse timing, and energy pulse coordinates on the posterior vaginal wall to induce remodeling of the subsurface region to treat urinary stress incontinence.

An embodiment of the invention relates to the system described above, where the distal end of the probe includes a treatment surface configured for non-invasive contact with the surface of the target tissue, the treatment surface has a width between 1 cm and 3 cm, and a length between 4 cm and 6 cm.

An embodiment of the invention relates to the system described above, where the distal end of the probe includes a first treatment surface and a second treatment surface spaced apart from the first treatment surface, the first and second treatment surface are spaced apart a distance equal to at least a width of a urethra.

The controller, including the integrated controllers described above, may include a display that is configured to display information about the procedure, the energy and/or heat, the coolant, the treatment tip, handle and other components of the system. This information may be displayed on the front of the integrated controller, and may present the information with audio signals as well. The display may also be used to display error information (including error codes) based on the status of the various system component (e.g., coolant level, contact with skin, RF generator status, etc.).

Embodiments relating to the system described above can include a power source. A power source in typical embodiments feeds energy to a power generator and power flows therefrom to the treatment tip. For example, utilizing RF, the RF waves can be produced in a range from 3 kHz to 300 GHz. A multiplexer measures current, voltage and temperature, at the thermal sensors associated with to each RF electrode. The multiplexer is driven by a controller, which can be a digital or analog controller, or a computer with software. The controller may turn the energy source and cooling source, if the treatment apparatus includes a cooling source, on and off. The controller may determine the length of each heating and/or cooling period in a given "pulse." The controller may provide multiple different types of pulses that may vary in the duration of heating or cooling. The controller may provide an indication that a pulse has ended, for example, by providing a visual or audio queue. When the controller is a computer it can include a CPU coupled through a system bus. On the system there may also be a keyboard, disk drive, or other non-volatile memory systems, a display, and other peripherals, as are well known in the art. Also coupled to the bus may be a program memory and a data memory.

An operator interface can include operator controls and a display. The controller can be coupled to different types of imaging systems including ultrasonic, thermal sensors, and impedance monitors. Current and voltage are used to calculate impedance. A diagnostic phase can be initially run to determine the level of treatment activity. This can be done through ultrasound as well as other means. Diagnostics can be performed both before and after treatment.

Methods

Methods for treating urinary stress incontinence in a subject according to some embodiment of the invention comprise non-invasive treatment of lower portions of the vagina. The lower portions of the vagina are the portions immediately inward from the introitus. An embodiment of the invention provides a non-surgical and non-invasive method for treating urinary stress incontinence by applying heat to a target area inside the vagina. In particular, the target tissue area is inside the vagina directly proximal to the hymenal ring and the application of heat to a target tissue induces remodeling of the target tissue. Thus, according to an embodiment of the invention, the portion of the vagina to be treated is a region between the hymen and a position located no further than about 4 to 6 cm inward from the hymen.

According to an embodiment of the invention, the anatomical areas of the female genitalia treated include the vagina and the introitus, the opening of the vagina. With more specific regard to the vagina, embodiments of the method comprise treating the lower portion of the vagina, a portion extending from the introitus to a location from about 4 cm to about 6 cm inward from the introitus. With regard to the circumference of the inner wall of the vagina, a clock-position reference scheme is helpful. FIG. 1 shows such a schematic, 136. The urethra lies next to the anterior wall of the vagina. Thus, the location of the vaginal wall nearest the urethra and urethral opening may be considered 12 o'clock in FIG. 1. With this reference point, the target tissues of embodiments of the invention include the approximately 90 degree arc between 10:30 and 1:30. Other target tissue regions include the approximately 60 degree arc between 5 o'clock and 7 o'clock. Some embodiments of the invention do not include treating the approximately 105 degree arc between 1:30 and 5 o'clock and the 105 degree arc between 7 o'clock and 10:30.

The vagina is a fibromuscular tube, lined with stratified squamous epithelium that connects the external and internal organs of the female reproductive system. The vagina runs obliquely upwards and backwards at an angle of about 45 degrees between the bladder in front and the rectum and anus behind. In an adult female the anterior wall is about 7.5 cm long and the posterior wall is about 9 cm long. The difference in length is due to the angle of insertion of the cervix through the anterior wall. FIG. 1 is a schematic view of female genitalia depicting the mucosal epithelial surfaces as well as an orienting clock 136 to provide a circumferential reference scheme for the vagina wall. FIG. 1 shows the urethra 130, Hart's line 120, the vaginal opening 122, the introitus 114, and the labium minora 126.

The mucosal epithelium of vulvar tissue outside the vagina and the introitus includes the labia minora, or that portion of the vulva extending outward from the introitus to Hart's line, the boundary where mucosal epithelium and labial skin meet. The mucosal epithelium and the skin, while contiguous, are embryologically and histologically distinct. The portion of the female genitalia that is covered by epithelium is also substantially defined by the bounds of the vestibule, which extends outward or down from the hymenal ring at the top of the vagina, radially beyond the introitus, including the portion of labia minora located within Hart's line 120. The target tissue of some embodiments of this invention include the connective tissue underlying these mucosal epithelial surfaces of the genitalia which, progressing down from the epithelial surface, are known as the lamina propria and the muscularis, respectively. The lamina propria includes a mixture of cell types that populate connective tissue, such as fibroblasts, and the muscularis is a layer of smooth muscle. Collagen is secreted or deposited into the extracellular space in these tissues by cells such as fibroblasts. These described target tissue layers below the epithelium overlay deeper tissues, including endopelvic fascia, which are not a target tissue for embodiments of the present invention.

The remodeling of the connective tissue underlying the mucosal epithelial surfaces does not substantially affect the epithelium itself. The method and apparatus, as provided by embodiments of the invention are non-invasive and substantially non-ablative of genital tissue. The nature of the engagement between the apparatus and genital tissue is that of contacting a treatment tip to an epithelial surface of the genital tissue. Through such contact, the apparatus delivers heat to underlying tissue, while preventing the heating of the surface epithelium by cooling it.

According to additional embodiments, with regard to the circumferential aspects of the vagina, heat may be applied to an area extending about 1.5-4 cm to (and more preferably 1.5-3 cm) the right of the urethra and about 1.5-4 cm (and more preferably 1.5-3 cm) to the left of the urethra on the anterior vaginal wall, excluding a region of about 0.5-1 cm in width along the urethra. Heat may further be applied to an area on the posterior vaginal wall mirroring the target areas on the anterior vaginal wall. In one embodiment, the method of treatment may include remodeling the target tissue in the target tissue areas shown in FIGS. 2A and 2B. The region on the posterior wall can extend about 4 cm (more preferably 3 cm) to the right of the midline and about 4 cm (more preferably 3 cm) to the left of the midline. In one embodiment, the method of treatment may include remodeling the target tissue in the target tissue areas shown in FIGS. 2A and 2B.

According to an embodiment of the invention, a "pulse" of energy is applied to a plurality of target locations. According to some embodiments, each pulse comprises a period of cooling of the target tissue, followed by a period of heating, and then a second period of cooling. The heating of target tissue, per some embodiments of the invention, includes raising the temperature of the target tissue to as high as 65 degrees C. The therapeutic temperature in some cases may be only as high as 45 degrees C. Per embodiments of the invention, target tissue may be heated to a temperature between about 48 degrees C. and about 65 degrees C. In other embodiments, the target tissue may be heated to a temperature between about 50 degrees C. and about 65 degrees C. In still other embodiments, the target tissue may be heated to a temperature between about 54 degrees C. and about 60 degrees C.

Figure 2A:
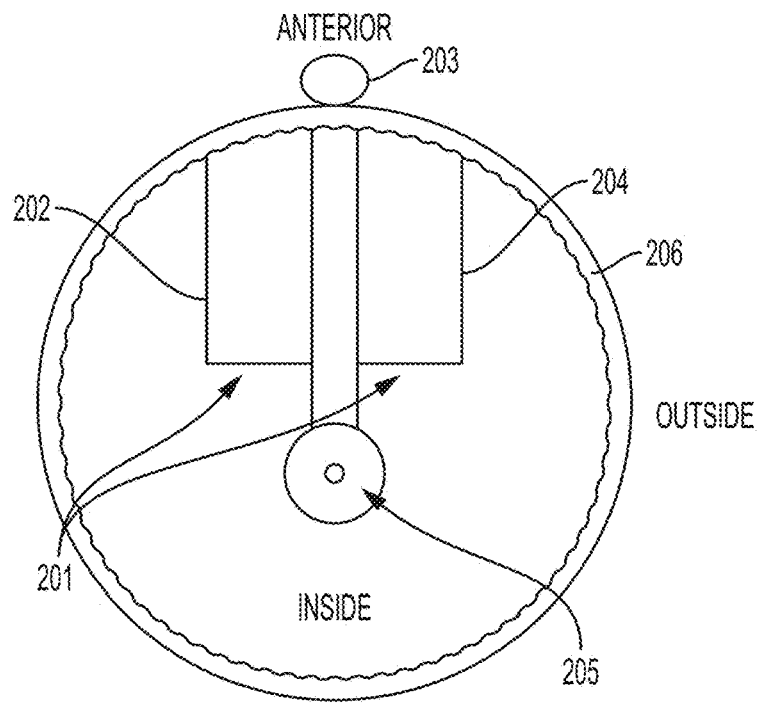
FIG. 2A is a schematic illustration of areas for treatment on the anterior vaginal wall.
Figure 2B:
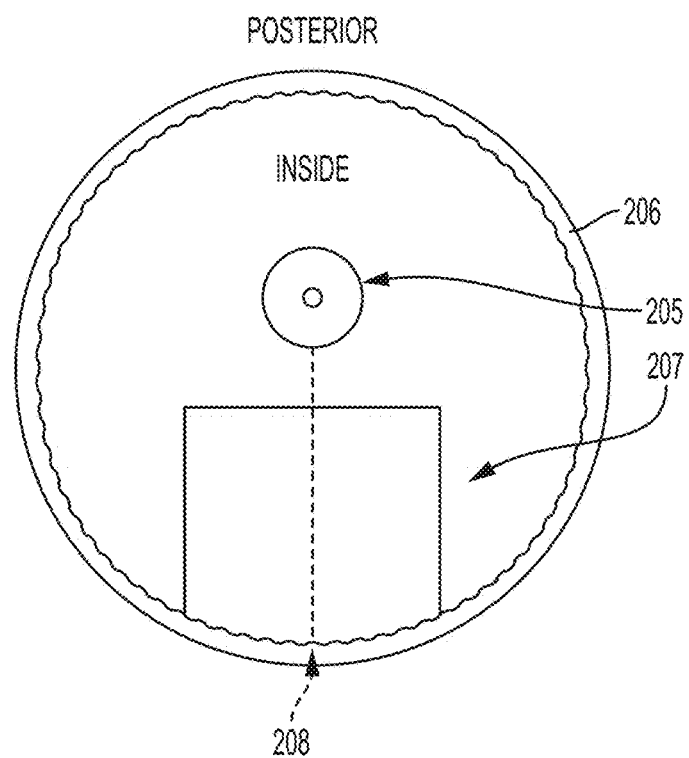
FIG. 2B is a schematic illustration of areas for treatment on the posterior vaginal wall.

An embodiment of the invention relates to a method for treating urinary stress incontinence in a subject by applying heat to the target tissues depicted in FIGS. 2A and 2B. FIGS. 2A and 2B shows two schematics, with FIG. 2A showing a cross-section of the vaginal canal and urethra and targeted tissues on the anterior wall, and FIG. 2B showing the vaginal canal and targeted tissues on the posterior wall. In such an embodiment, heat is applied to a subsurface region of a target tissue 201 to a predetermined temperature for a period of time sufficient to induce remodeling of the subsurface region. The heating step includes heating at least part of a first portion of the subject's vagina 202, the first portion located on an anterior vaginal wall extending from about 0.25 cm to the left of the subject's urethra 203 to about 2 cm to the left of the subject's urethra. The heating step also includes heating at least part of a second portion of the subject's vagina 204, the second portion located on the anterior vaginal wall extending from about 0.25 cm to the right of the urethra to about 2 cm to the right of the urethra 203. The heating includes heating a portion of the vagina extending from the hymen inwardly towards the cervix 205 to a location from 4.0 cm to 6.0 cm from the hymen 206. The method also includes heating at least part of a third portion of the subject's vagina 207, wherein the third portion is located on a posterior vaginal wall extending from about 3.0 cm to the left of a midline 208 to about 3.0 cm to the right of the midline.

According to some embodiments of the invention, a plurality of radiofrequency pulses is delivered to the target tissue areas 201 shown in FIG. 2A. The anterior vaginal wall can be treated with a first pulse of energy directly to the left of the urethra 203 (patient's right). The second pulse is delivered 0.5 cm to the left of the first pulse. The third pulse is delivered directly proximal to the hymenal ring 206 and directly to the right of the urethra, and the fourth pulse is delivered 0.5 cm to the right of the third pulse. The fifth to eighth pulses are delivered in similar locations to the first four pulses, but in this case 1.5 cm proximal to the hymenal ring, i.e., further into the vagina. The ninth pulse is delivered proximal to the hymenal ring and directly to the left of the midline 208 on the posterior vaginal wall. The tenth and eleventh pulses are delivered to the left of the ninth pulse, 0.5 cm and 1.0 cm, respectively, from the ninth pulse. The twelfth, thirteenth, and fourteenth pulses are delivered in a similar manner as pulses nine through eleven, but starting directly to the right of the midline on the posterior vaginal wall and then moving 0.5 cm to the right each time. The fifteenth through twentieth pulses are delivered in similar locations as the ninth through fourteenth pulses, but located 1.5 cm proximal to the hymenal ring, i.e., further into the vagina.

Figure 3A:
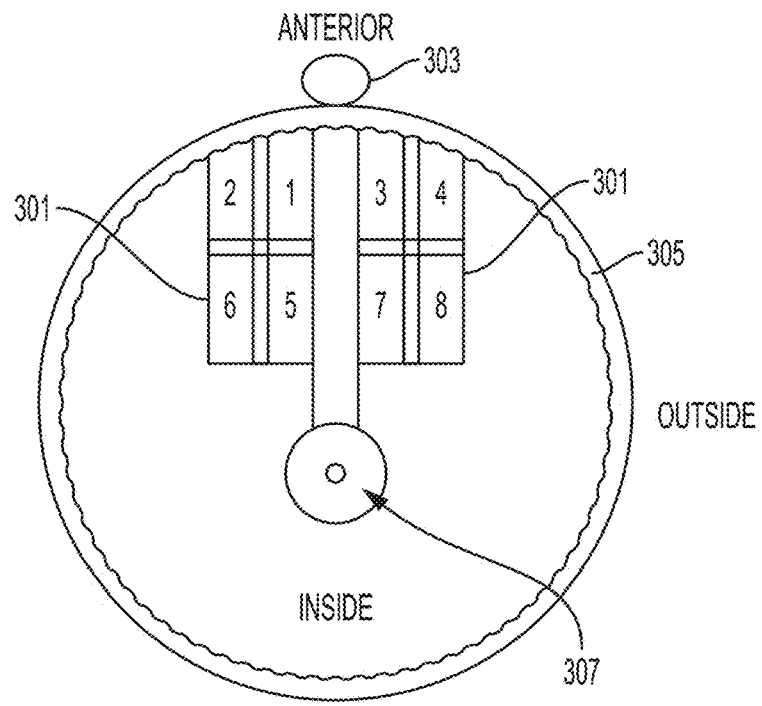
FIG. 3A is a schematic illustration of eight locations for the application of pulses by a treatment tip on the anterior vaginal wall according to some embodiments of the invention.
Figure 3B:
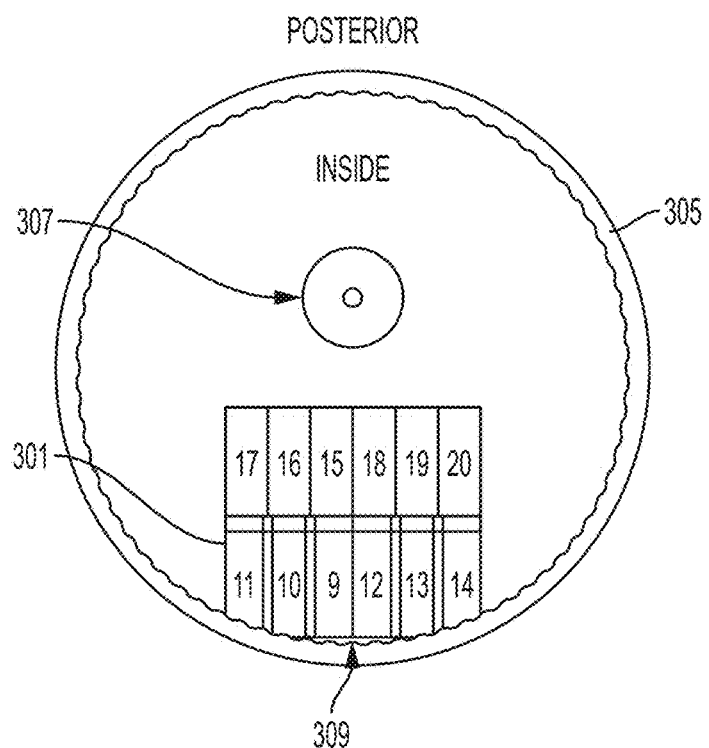
FIG. 3B is a schematic illustration of twelve locations for the application of pulses by a treatment tip on the posterior vaginal wall according to some embodiments of the invention.

According to some embodiments of the invention, the pulses can be applied sequentially, as illustrated in FIGS. 3A-3D. FIGS. 3A and 3B show two schematics, with FIG. 3A representing a schematic showing a cross-section of the vaginal canal and urethra and targeted tissues on the anterior wall, and FIG. 3B showing the vaginal canal and targeted tissues on the posterior wall. In such embodiments, a portion of some pulses may overlap with a portion of one or more other pulses, also as shown in FIGS. 3A and 3B. The sequence of pulses may be repeated five times, for a total of 100 pulses. In FIGS. 3A and 3B, the relative positions of the various target tissue areas 301 within the vaginal canal are shown. Also shown, for orientation, is the urethral opening 303, the hymen 305, the cervix 307 and the midline 309. The pulses may be applied in the sequence indicated by the numbering in FIGS. 3A and 3B. However, the embodiments of the invention are not limited to this sequence.

Figure 3C:
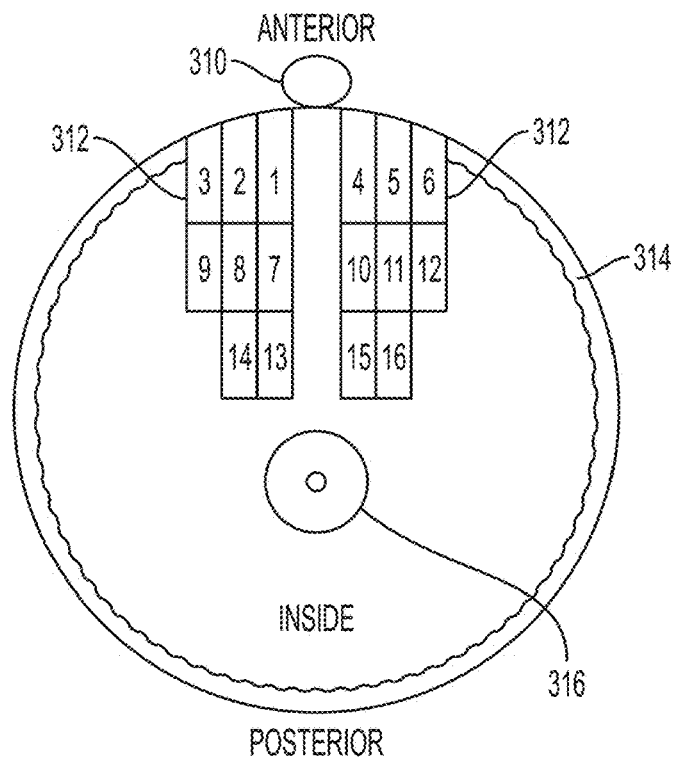
FIG. 3C is a schematic illustration of sixteen locations for the application of pulses by a treatment tip on the anterior vaginal wall according to some embodiments of the invention.
Figure 3D:
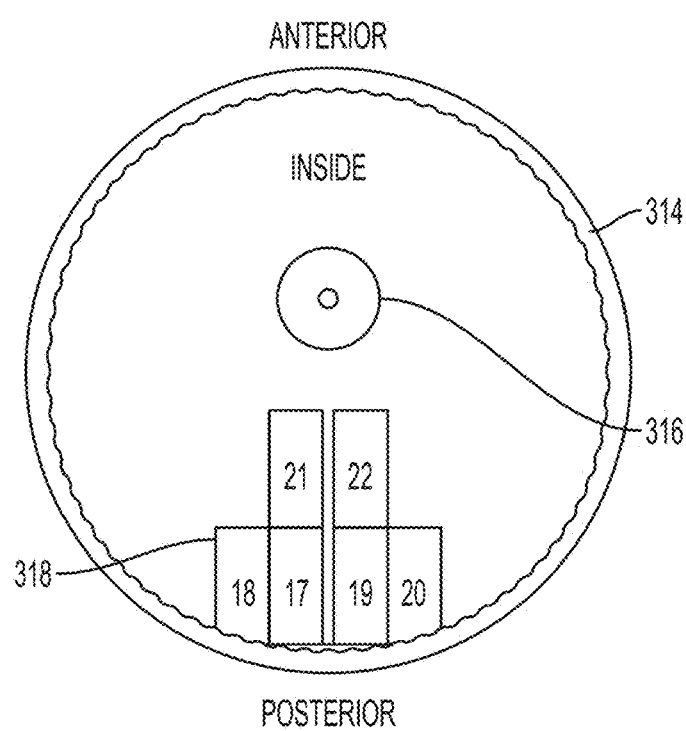
FIG. 3D is a schematic illustration of six locations for the application of pulses by a treatment tip on the posterior vaginal wall according to some embodiments of the invention.

FIGS. 3C and 3D show two additional schematics, with FIG. 3C representing a cross-section of the vaginal canal and urethra and targeted tissues on the anterior wall, and FIG. 3D showing the vaginal canal and targeted tissues on the posterior wall. In such embodiments, a portion of some pulses may overlap with a portion of one or more other pulses, also as shown in FIGS. 3C and 3D. The sequence of pulses may be repeated five times, for a total of 110 pulses. In FIGS. 3C and 3D, the relative positions of the various target tissue areas 312, 318 within the vaginal canal are shown. Also shown, for orientation, is the urethral opening 310, the hymen 314, and the cervix 316. The pulses may be applied in the sequence indicated by the numbering in FIGS. 3C and 3D. However, the embodiments of the invention are not limited to this sequence.

A system for treating urinary stress incontinence includes a urinary stress incontinence treatment parameter that may include an anterior vaginal energy output parameter. The anterior vaginal energy output parameter may achieve the treatment illustrated in FIGS. 3A and 3C, for example. The anterior vaginal energy output parameter is configured as an energy transfer sequence comprising energy pulse duration, energy pulse timing, and energy pulse coordinates on the anterior vaginal wall to induce remodeling of the subsurface region to treat urinary stress incontinence. For example, the energy transfer sequence may include the application of energy to region 301 in FIG. 3A and region 312 in FIG. 3C. The locations identified by numbers 1-8 in FIG. 3A and 1-16 in FIG. 3C are example energy pulse coordinates. Example of the energy pulse duration and energy pulse timing are provided below. See, for example, FIG. 5 and discussion thereof. Other energy pulse coordinates, durations, and timings, including but not limited to those described herein, can also be used.

The urinary stress incontinence treatment parameter according to some embodiments includes a posterior vaginal energy output parameter. The posterior vaginal energy output parameter may achieve the treatment illustrated in FIGS. 3B and 3D, for example. The posterior vaginal energy output parameter is configured as an energy transfer sequence comprising energy pulse duration, energy pulse timing, and energy pulse coordinates on the posterior vaginal wall to induce remodeling of the subsurface region to treat urinary stress incontinence. For example, the energy transfer sequence may include the application of energy to region 301 in FIG. 3B and region 318 in FIG. 3D. The locations identified by numbers 9-20 in FIG. 3B and 17-22 in FIG. 3D are example energy pulse coordinates. Example of the energy pulse duration and energy pulse timing are provided below. See, for example, FIG. 5 and discussion thereof. Other energy pulse coordinates, durations, and timings, including but not limited to those described herein, can also be used.

The sequence of twenty pulses is exemplary, and the order of the pulses is not limited to the sequence described above. The description provided herein details an exemplary method of applying overlapping pulses to substantially cover the target treatment area. The extent to which the pulses overlap, as well as the number of pulses used to cover the target tissue area, may depend on the size of the energy delivery element that is used to apply radiofrequency energy to the target tissue. The above-described sequence of pulses can be used for an energy delivery element having a width of approximately 1 cm, and a length of approximately 2.5 cm. Devices having a larger or smaller energy delivery element may also be employed, though a smaller energy delivery element may require a greater number of pulse locations in order to cover the target tissue area.

An embodiment of the invention relates to a method for treating urinary stress incontinence in a subject. The method includes the steps of: a first cooling step for cooling a surface region of a target tissue for a first period of time; a heating step for heating a subsurface region of the target tissue to a predetermined temperature for a second period of time sufficient to induce remodeling of the target tissue; and a second cooling step for cooling the surface region of the target tissue for a third period of time. The first period of time is shorter than the third period of time, the heating comprises delivering energy by contacting an epithelial tissue layer in the subject's vagina with a treatment tip, the tip including an energy delivery element, and the heating includes heating a portion in the subject's vagina extending from the hymen inwardly to a location from 4.0 cm to 6.0 cm from the hymen. In such embodiments, the combination of the first cooling step, the heating step and the second cooling step comprises a "pulse." In such a pulse, the first period of time can be up to 4 seconds in length, and more preferably about 0.5 seconds in length. The heating step can be between 1 and 5 seconds in length, and more preferably between 2 and 4 seconds in length. The cooling step can be longer than 4 seconds in length, and more preferably about 4 seconds in length. The second cooling step is longer than the first cooling event so that the temperature of the target tissue following the heating step is prevented from remaining elevated beyond a desired amount of time. Such an elevation can occur because the subsurface tissue can continue to radiate heat even after the heating period has ended. In such instance, cooling can be used to ensure that the temperature of the surface tissue does not rise too much or beyond the therapeutic temperature.

Figure 4:
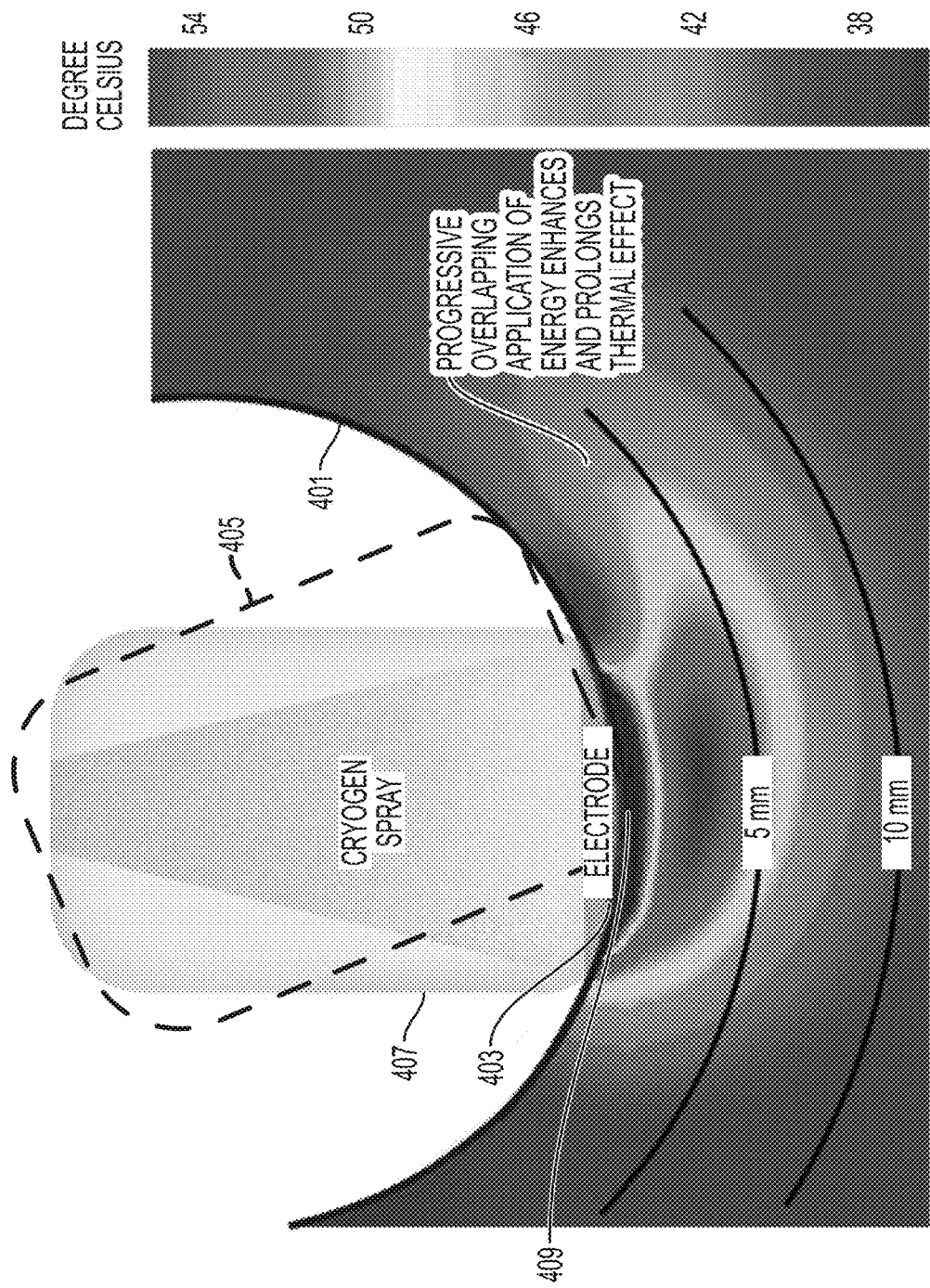
FIG. 4 is a model representing nominal tissue parameters and depicting sample pulse positions, and showing the thermal effect induced by the progressive overlapping application of energy and the reverse thermal gradient.

FIG. 4 is a schematic showing application of two "pulse" events during a therapeutic session, according to an embodiment of the invention. In FIG. 4, the vaginal wall 401 of a target area is contacted with a treatment tip 403 at a first position 405 and subsequently a second position 407. In such an embodiment, a cooling step occurs before and after a heating step. During each pulse, a reverse thermal gradient is created from the cooling-heating-cooling pulse sequence 409 with the surface tissues treated at a lower temperature than the subsurface tissues. The heating step results in heating of subsurface tissues to a desired therapeutic temperature. The desired therapeutic temperature is between 45 degrees C. to 65 degree C. The subsurface tissue targeted by the heating step resides at least 1 mm from the surface. In some embodiments, tissue as far as 10 mm beneath the surface is targeted. The heating is done by applying energy from an energy source (such as a radiofrequency energy source, for example) to the subsurface tissues. The application a cooling-heating-cooling pulse sequence to adjacent or overlapping positions (as depicted in FIG. 4) results in the enhancement and prolongation of the thermal effect on the target tissues.

Figure 5:
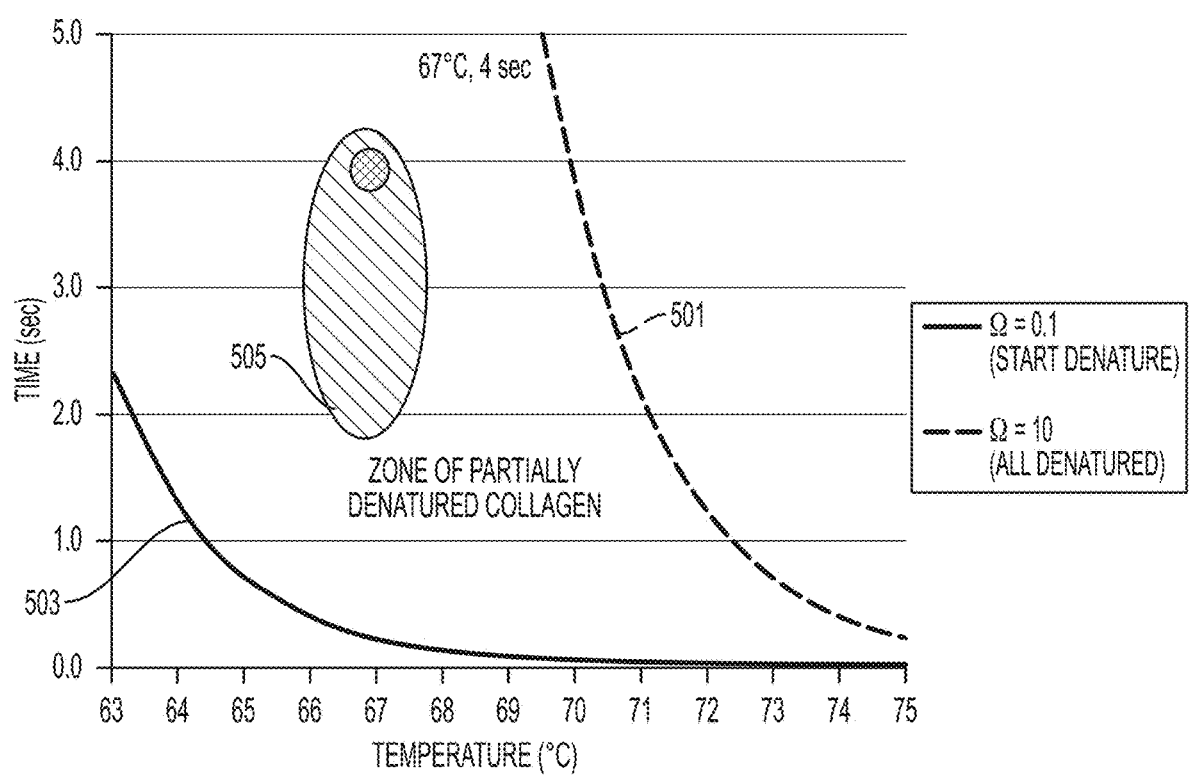
FIG. 5 is a graph showing the thermal dose that may be required for partially and fully denaturing collagen.

The temperature to which the target tissue is to be raised during a heating step as well as the duration of the heating step according embodiments of the current invention are determined by the amount of time required for the partial or complete denaturing of collagen in the target tissue at a particular temperature. FIG. 5 shows a graph that is used to determine such parameters. In FIG. 5, the region between the line indicating parameters required for the full denaturing of collagen 501 and the line indicating the initiation of the denaturing of collagen 503 is the zone of partially denatured collagen. Some embodiments of the instant invention involve the heating of a target tissue up to about 67 degrees Celsius for between about 2 to 4 seconds, as depicted by the darkened oval 505. This results in the partial denaturing of collagen. Some embodiments of the instant invention involve the heating of a target tissue to a temperature that is less than 67 degrees Celsius. This may initiate a release of heat shock proteins that results in strengthening of the tissue without denaturing collagen.

Some embodiments of the invention heat the target tissue to a temperature below that required for total denaturing of collagen and for a duration of time less than that required for the denaturing of collagen. FIG. 5 details the temperatures and lengths of time needed for complete denaturing of collagen. Embodiments of the instant invention aim to increase the generation of collagen in the target tissue via anabolic repair versus catabolic repair. It is understood that a difference between anabolic versus catabolic repair is that catabolic repair occurs after catastrophic tissue damage and collagen denaturing. Anabolic repair, by contrast, occurs when the tissue is not severely damaged and when not all of the collagen has been denatured.

A system for treating urinary stress incontinence includes at least one urinary stress incontinence treatment parameter, which may be selected to achieve a predetermined temperature for a predetermined time period. The predetermined temperature and predetermined time period may be sufficient to achieve remodeling of the target tissue. In some cases, the remodeling includes inducing at least partial degradation of collagen within the target tissue. Example predetermined temperatures are temperatures of at least 48 C degrees. Example predetermined temperatures according to some embodiments are temperatures between 50 C degrees and 65 C degrees. Predetermined time periods for maintaining the predetermined temperature are between 1 second and 5 seconds. According to some embodiments, the predetermined time period is 2 seconds.

Figure 6A:
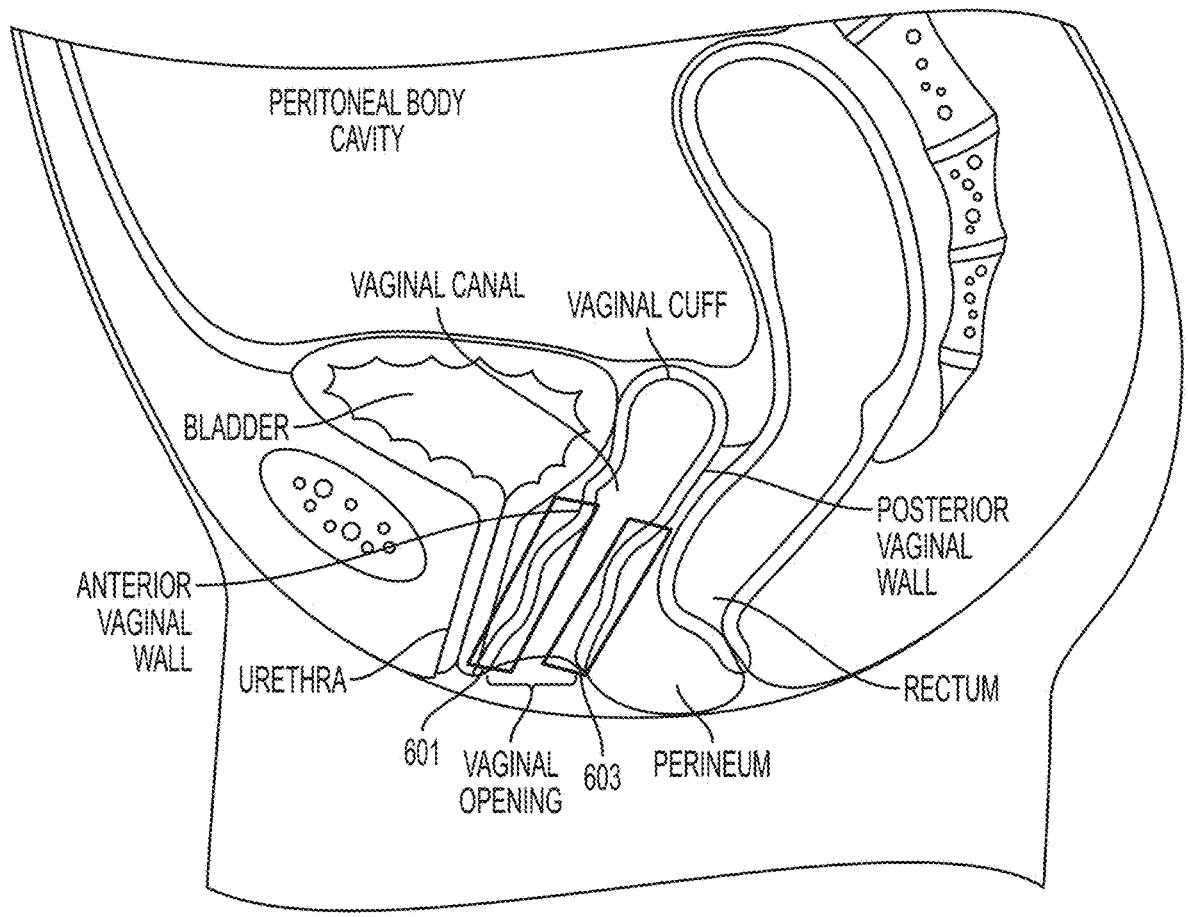
FIG. 6A is a schematic showing a cross-sectional view of the female bladder, urethra, and vaginal canal taken along the sagittal plane as well as other anatomical structures and showing representative treatment areas.
Figure 6B:
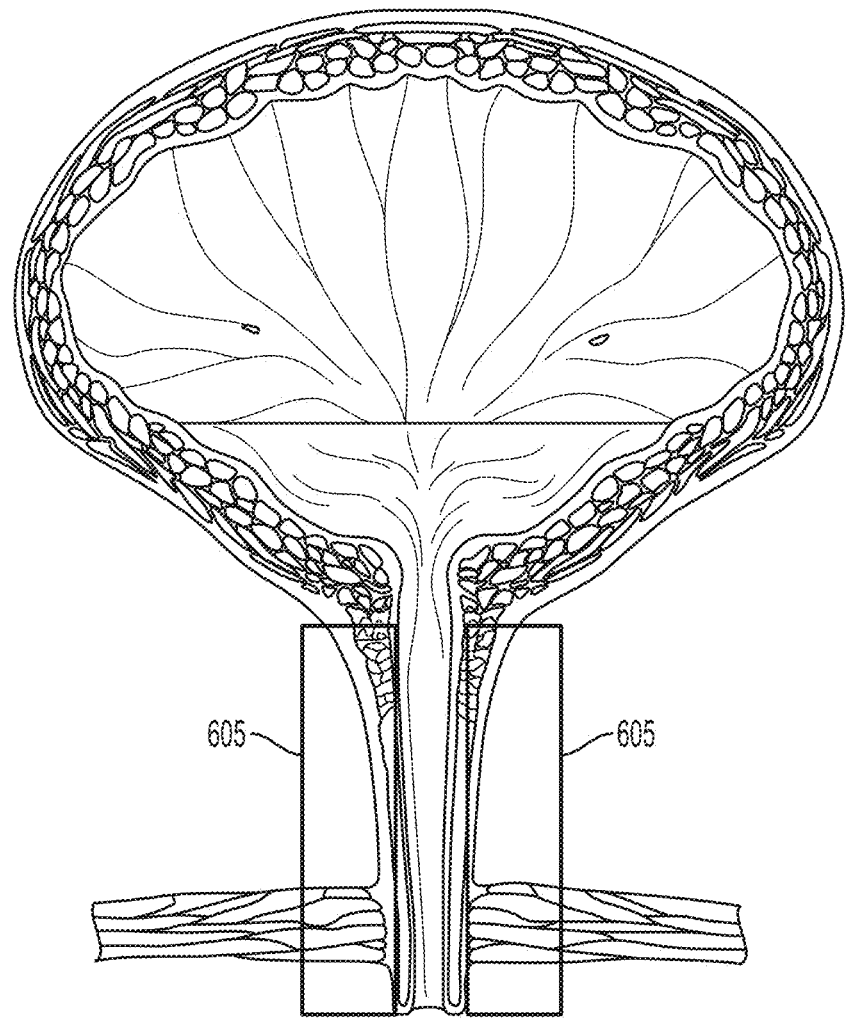
FIG. 6B is a schematic showing a cross-sectional view of the female bladder taken along the coronal plane and showing representative treatment areas.

According to an embodiment of the invention, subsurface tissues in the vaginal canal located adjacent to and around the bladder neck and urethra are targeted increased collagen regeneration. As seen in FIGS. 6A and 6B, the treatment is focused on the subsurface tissues of a portion of an anterior wall of the vaginal canal that runs adjacent to (but not directly over) the length of a urethra and bladder neck 601. This area represents an area of 4-6 cm from the hymen towards the cervix. Subsurface tissues of a portion of a posterior wall 603 diametrically opposed to the anterior wall being treated are also targeted for therapy. FIG. 6A is a schematic showing a cross-sectional view of the female bladder, urethra, and vaginal canal taken along the sagittal plane as well as other anatomical structures and showing representative treatment areas. FIG. 6B is a schematic showing a cross-sectional view of the female bladder taken along the coronal plane and showing representative treatment areas 605 treated by a method relating to an embodiment of the instant invention.

In accordance with the principles of the invention, firming of the tissue in the targeted treatment zones in the vicinity of the urethra and bladder neck provides for treatment of urinary stress incontinence. In certain aspects of the invention, the treatment may not lift the urethra or change its position in any way. Treatment can be carried out with the intention of firming the tissue beside the urethra and under the bladder neck so that when a subject coughs or sneezes there is less downward movement of the bladder neck. The firming of the tissues can be done by increasing the density of the collagen in the treated tissue. Increased collagen generation can be induced by heating of the target tissues in accordance with the principles of the invention. However, other embodiments and implementations may lift or change the position of the urethra and/or bladder neck.

According to an embodiment of the invention, a single treatment session follows the protocol outlined in Table 1.

TABLE 1

Treatment Protocol

| | Treatment Protocol | | | | |
|---|---|---|---|---|---|
| Repetition | Radial "Clock" Position (with urethra as 12 o'clock) | Distance Inside Hymenal Ring | | | Total # of Pulses per Pass | Total # of Pulses per Treatment |
| | | ~2 cm | ~3.5 cm | ~5 cm | | |
| Repeat 5 times | 12:30 | 1x | 1x | 1x | 3 | 15 |
| | 1:00 | 1x | 1x | 1x | 3 | 15 |
| | 1:30 | 1x | 1x | | 2 | 10 |
| | 11:30 | 1x | 1x | 1x | 3 | 15 |
| | 11:00 | 1x | 1x | 1x | 3 | 15 |
| | 10:30 | 1x | 1x | | 2 | 10 |
| Repeat 5 times | 5:00 | 1x | | | 1 | 5 |
| | 5:30 | 1x | 1x | | 2 | 10 |
| | 6:30 | 1x | 1x | | 2 | 10 |
| | 7:00 | 1x | | | 1 | 5 |

In the treatment protocol outlined in Table 1, each "pulse" includes a first cooling step, a heating step, and a second cooling step. The temperature of the target tissue during the heating step is greater than or equal to 48 degrees C. and the duration of the heating step is between 1 to 5 seconds. According to some embodiments, the duration of the heating step is 2 seconds. In a system for treating urinary stress incontinence, a urinary stress incontinence treatment parameter is selected to achieve the predetermined temperature and the predetermined time period. For example, the urinary stress incontinence treatment parameter is selected to achieve a tissue temperature of at least 48 degrees for a time period of 1 to 5 seconds. These values are non-limiting example, and urinary stress incontinence treatment parameters may be selected to achieve other predetermined temperatures for other predetermined time periods in the target tissue to induce remodeling of the target tissue.

The target tissues are located between 10:30 and 1:30 anteriorly (avoiding the urethra) and between 5 o'clock and 7 o'clock (posteriorly). Each target area within the target tissues is "pulsed" at least 5 times, with areas adjacent to the urethra (residing at 12:30 o'clock and 1:00 o'clock) being pulsed 15 times. Multiple pulses may be administered in sequence, i.e., in a single pass. Alternatively, for some locations, only a single pulse is administered per pass. A pass may include delivering one or more pulses to all of the treatment locations, or to only a subset of the treatment locations. A treatment session may include multiple passes. In the example shown in Table 1, the treatment session includes 5 passes.

In the treatment discussed above, the first cooling step is between 0.5 to 3.5 seconds, more preferably 0.5 seconds. The second cooling step proceeds the heating step and between 3.5 to 10 seconds, more preferably 4 seconds. The first cooling steps protects the surface tissues from damage during the heating step. The second cooling step protects the surface tissues from residual heat radiated from the surface tissues following the heating step. Also, the second heating step serves to lower the temperature of the surface tissue so as to prevent unintended damage to these tissues due to the heating step.

Cooling can be provided and can be applied in a burst or continuous manner. Cooling is described in assignee's U.S. Pat. No. 9,271,785, which is incorporated herein by reference in its entirety.

Figure 7:
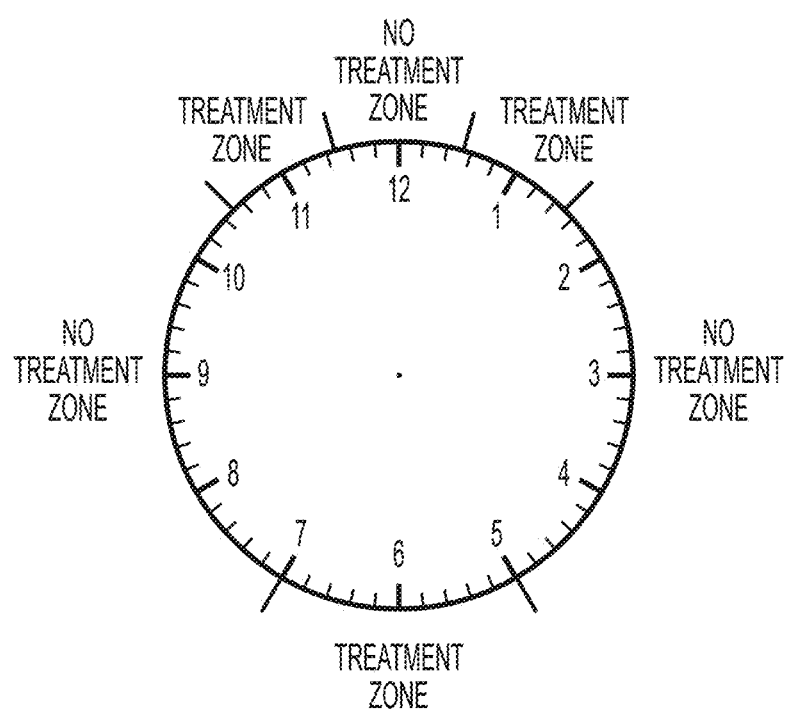
FIG. 7 is a schematic of an orienting clock to provide a circumferential reference scheme for the vaginal wall with treatment zones and no treatment zones indicated according to an embodiment of the invention.

FIG. 7 is a schematic of an orienting clock to provide a circumferential reference scheme for the vaginal wall with treatment zones and no treatment zones according to the protocol of Table 1. The urethra is located near the anterior vaginal wall at about 12 o'clock, and the center of the posterior vaginal wall is located at 6 o'clock.

In some embodiments, remodeling of the tissues on the anterior wall of the vaginal canal results in collagen denaturing and neo-collagenesis. This has the effect of buttressing the tissues adjacent to and comprising the urethra. Unlike traditional methods of supporting the tissues of the urethra to treat or alleviate urinary stress incontinence, the instant buttressing effect is achieved sans introduction of materials not native to the vaginal canal or urethra and sans the necessity to bridge such materials to regions neighboring or removed from the urethra or vaginal canal.

The ability of the instant methods to achieve efficient buttressing of the tissues adjacent to and comprising the urethra sans introduction of materials not native to the vaginal canal or urethra and sans the necessity to bridge such materials to regions neighboring or removed from the urethra or vaginal canal represents a novel and unexpected finding. It would not be expected that adequate support to the tissues adjacent to and comprising the urethra could be achieved simply by treating tissues of the anterior wall of the vaginal canal such that these tissues are provoked into producing enough collagen to efficiently support the urethra and neck of the bladder to alleviate and treat urinary stress incontinence. Current methods to treat urinary stress incontinence rely on invasive procedures to apply non-native materials or meshes to and/or around the tissues of the urethra to act as a support bridge. These materials or meshes must be connected laterally to tissues adjacent to the urethra or bladder. The instant methods requires no such invasive procedures nor lateral connection points.

In some embodiments, tissues on the posterior side of the vaginal canal diametrically opposed to the anterior vaginal canal adjacent to the urethra are targeted for collagen denaturing and neo-collagenesis by heating. This is done to provide further support to the anterior wall of the vaginal canal since the anterior wall and the posterior wall are in close proximity to one another anatomically. Remodeling of the posterior wall of the vaginal canal provides further support against urinary stress incontinence during strenuous events such as coughing, sneezing or other activities involving contraction of muscles in and around the vagina and abdomen.

The tissue targeted is subsurface tissue residing at least 1 mm beneath the surface tissue and up to 8 mm beneath the surface tissue. The maximum vaginal depth of the target tissue is 6 cm beyond the hymen. Heating according to some embodiments is accomplished by delivering radiofrequency energy via a device having a treatment tip configured to deliver radiofrequency energy. The treatment tip can take on a variety of shapes and has a surface area contacting the vaginal wall of greater than or equal to 2 cm$^2$. A subsequent treatment can be performed within one month, or at a time later than one month.

In one embodiment of the invention, lateral regions of the vaginal canal (corresponding to regions between 1 o'clock to 5 o'clock and between 7 o'clock to 11 o'clock) are also targeted. Targeting such areas is especially relevant when combining the instant methods with general vaginal remodeling methods.

An embodiment of the invention relates to a method for treating urinary stress incontinence in a subject. The method includes the steps of: non-invasively heating a subsurface region of a target tissue to a temperature for a period of time sufficient to induce a remodeling of the subsurface region; and inducing remodeling of the subsurface region to treat urinary stress incontinence.

An embodiment of the invention relates to a method for treating urinary stress incontinence in a subject as described above, where the step of inducing remodeling of the subsurface region further includes inducing positioning of a urethra to treat urinary stress incontinence.

An embodiment of the invention relates to a method for treating urinary stress incontinence in a subject as described above, where the step of non-invasively heating further includes heating to at least one of a predetermined temperature for a predetermined period of time to induce remodeling of the subsurface region to treat urinary incontinence.

An embodiment of the invention relates to a method for treating urinary stress incontinence in a subject as described above, where the step of non-invasively heating further includes heating an anterior vaginal wall proximate and apart from a urethra of the subject, and avoiding directly heating the urethra to the temperature, and inducing remodeling of the subsurface region to create a buttress of remodeled tissue to support the urethra to treat urinary stress incontinence.

An embodiment of the invention relates to a method for treating urinary stress incontinence in a subject as described above, where the step of non-invasively heating includes heating an anterior vaginal wall proximate and apart from a urethra of the subject and heating a posterior vaginal wall substantially diametrically opposed to the heated anterior vaginal wall, the sidewalls between the anterior and posterior vaginal walls remain untreated with heat.

An embodiment of the invention relates to a method for treating urinary stress incontinence in a subject as described above, where the step of non-invasively heating further includes heating a posterior vaginal wall, inducing remodeling of the subsurface region of the posterior vaginal wall to treat urinary stress incontinence by the remodeled vaginal wall providing a buttress of remodeled tissue to support an anterior vaginal wall when compressed against the posterior vaginal wall.

An embodiment of the invention relates to a method for treating urinary stress incontinence in a subject as described above, where the method further includes the step of cooling the target tissue.

An embodiment of the invention relates to a method for treating urinary stress incontinence in a subject as described above, where the step of non-invasively heating includes: heating at least part of a first portion of a vagina of the subject, the first portion located on an anterior vaginal wall extending from about 0.25 cm to a left of a urethra of the subject to about 2 cm to the left of the urethra; and heating at least part of a second portion of the vagina, the second portion located on the anterior vaginal wall extending from about 0.25 cm to the right of the urethra to about 2 cm to the right of the urethra. The non-invasively heating includes heating a portion of the vagina extending from a hymen inwardly to a location from 4.0 cm to 6.0 cm from the hymen.

An embodiment of the invention relates to a method for treating urinary stress incontinence in a subject as described above, where the step of non-invasively heating the target tissue further includes heating at least part of a third portion of the vagina. The third portion is located on a posterior vaginal wall extending from about 3.0 cm to a left of a midline to about 3.0 cm to a right of the midline.

An embodiment of the invention relates to a method for treating urinary stress incontinence in a subject as described above, where any tissue residing outside of the first portion, the second portion or the third portion is not treated.

An embodiment of the invention relates to a method for treating urinary stress incontinence in a subject as described above, where the step of non-invasively heating includes heating the target tissue to a temperature between 45 degrees C. and 65 degrees C.

An embodiment of the invention relates to a method for treating urinary stress incontinence in a subject as described above, where the step of non-invasively heating includes heating the target tissue to a temperature between 54 degrees C. and 60 degrees C.

An embodiment of the invention relates to a method for treating urinary stress incontinence in a subject as described above, where the step of non-invasively heating further includes delivering of at least one of radiofrequency energy, microwave energy, laser energy, or ultrasound energy.

An embodiment of the invention relates to a method for treating urinary stress incontinence in a subject as described above, where the period of time sufficient to induce remodeling of the subsurface region is between 1 second to 5 seconds.

An embodiment of the invention relates to a method for treating urinary stress incontinence in a subject as described above, where the period of time sufficient to induce remodeling of the subsurface region is between 2 seconds to 4 seconds.

An embodiment of the invention relates to a method for treating urinary stress incontinence in a subject as described above, where the step of non-invasively heating further includes heating a submucosa tissue layer.

An embodiment of the invention relates to a method for treating urinary stress incontinence in a subject as described above, where a step of cooling a surface region of the target tissue is included.

An embodiment of the invention relates to a method for treating urinary stress incontinence in a subject as described above, where the cooling of the surface region of the target tissue includes contacting an epithelial tissue layer of the target tissue with a treatment tip, the treatment tip including a cooling mechanism.

An embodiment of the invention relates to a method for treating urinary stress incontinence in a subject as described above, where the cooling of the surface region includes cooling the epithelial tissue layer to a temperature between 0 degrees C. and 10 degrees C.

An embodiment of the invention relates to a method for treating urinary stress incontinence in a subject as described above, where a step of contacting an epithelial tissue layer of a vagina of the subject with a treatment tip at two or more contact sites during a procedure is included. The treatment tip includes an energy delivery element adapted to non-invasively heat the target tissue.

An embodiment of the invention relates to a method for treating urinary stress incontinence in a subject as described above, where the step of contacting an epithelial tissue layer of the vagina with a treatment tip at two or more contact sites is repeated at least twice during the procedure such that each of the two or more contact sites is contacted at least twice.

An embodiment of the invention relates to a method for treating urinary stress incontinence in a subject as described above, where the step of contacting an epithelial tissue layer of the vagina with a treatment tip at two or more contact sites is repeated at least five times during the procedure such that each of the plurality of contact sites is contacted at least five times.

An embodiment of the invention relates to a method for treating urinary stress incontinence in a subject as described above, where the remodeling includes at least one of contracting target tissue, denaturing collagen, tightening collagen-rich sites in the target tissue, or releasing heat shock proteins.

An embodiment of the invention relates to a method for treating urinary stress incontinence in a subject as described above, where at least some of the remodeling occurs during the step of non-invasively heating.

An embodiment of the invention relates to a method for treating urinary stress incontinence in a subject as described above, where including cooling a surface region of the target tissue for a first period of time; and cooling the surface region of the target tissue for a second period of time. The first period of time is shorter than the second period of time. The step of non-invasively heating includes delivering energy by contacting an epithelial tissue layer in a vagina of the subject with a treatment tip, the treatment tip including an energy delivery element. The step of non-invasively heating includes heating a portion in the vagina extending from a hymen inwardly to a location from 4.0 cm to 6.0 cm from the hymen.

An embodiment of the invention relates to a method for treating urinary stress incontinence in a subject as described above, where the step of non-invasively heating further includes heating a submucosa tissue layer. The step of cooling of the surface region of the target tissue for a first period of time further includes cooling an epithelial tissue layer, and the step of cooling of the surface region of the target tissue for a second period of time further includes cooling the epithelial tissue layer.

An embodiment of the invention relates to a method for treating urinary stress incontinence in a subject as described above, where the step of cooling of the surface region of the target tissue for a first period of time and the step of cooling of the surface region of the target tissue for a second period of time each further include contacting an epithelial tissue layer with a treatment tip, the treatment tip including a cooling mechanism.

An embodiment of the invention relates to a method for treating urinary stress incontinence in a subject as described above, where the step of cooling of the surface region of the target tissue for a first period of time and the step of cooling of the surface region of the target tissue for a second period of time each further include cooling the surface region of the target tissue to a temperature between 0 degrees C. and 10 degrees C.

An embodiment of the invention relates to a method for treating urinary stress incontinence in a subject as described above, where the step of non-invasively heating includes heating at least part of a first portion of a vagina of the subject circumferentially around a wall of the vagina from 11 o'clock to 1 o'clock. An aspect closest to a urethra of the subject is 12 o'clock.

An embodiment of the invention relates to a method for treating urinary stress incontinence in a subject as described above, where the step of non-invasively heating further includes heating a portion of the vagina extending from a hymen inwardly to a location from 4.0 cm to 6.0 cm from the hymen.

An embodiment of the invention relates to a method for treating urinary stress incontinence in a subject as described above, where the step of non-invasively heating further includes heating at least part of a second portion of the subject's vagina circumferentially around a wall of the subject's vagina between 5 o'clock to 7 o'clock, and the second portion is diametrically opposed to the first portion.

An embodiment of the invention relates to a method for treating urinary stress incontinence in a subject as described above, where any tissue residing outside of the first portion or the second portion is not treated.

An embodiment of the invention relates to a method for treating urinary stress incontinence in a subject as described above, where the step of non-invasively heating includes one of: heating the target tissue to a temperature between 45 degrees C. and 65 degrees C.; and heating the target tissue to a temperature between 54 degrees C. and 60 degrees C.

An embodiment of the invention relates to a method for treating urinary stress incontinence in a subject as described above, where the period of time sufficient to induce remodeling of the target tissue is one of: between 1 second to 5 seconds and between 2 seconds to 4 seconds.

An embodiment of the invention relates to a method for treating urinary stress incontinence in a subject as described above, where the method includes a step for cooling a surface region of the target tissue. The cooling of the surface region of the target tissue includes contacting an epithelial tissue layer of the target tissue with a treatment tip, the treatment tip including a cooling mechanism.

An embodiment of the invention relates to a method for treating urinary stress incontinence in a subject as described above, where the method includes cooling the surface region of the target tissue by cooling the epithelial tissue layer to a temperature between 0 degrees C. and 10 degrees C.

An embodiment of the invention relates to a method for treating urinary stress incontinence in a subject as described above, where the step of non-invasively heating includes at least one of heating at least part of a second portion of the vagina circumferentially around a wall of the vagina between 1 o'clock to 5 o'clock and heating at least part of a second portion of the vagina circumferentially around a wall of the vagina between 7 o'clock to 11 o'clock.

An embodiment of the invention relates to a method for non-invasively treating urinary stress incontinence in a subject. The method includes the steps of: heating a subsurface region of a target tissue to a predetermined temperature for a period of time sufficient to induce remodeling of the subsurface region. The heating step involves: heating at least part of a first portion of the subject's vagina, the first portion located on an anterior vaginal wall extending from about 0.25 cm to the left of the subject's urethra to about 2 cm to the left of the subject's urethra; and heating at least part of a second portion of the subject's vagina, the second portion located on the anterior vaginal wall extending from about 0.25 cm to the right of the urethra to about 2 cm to the right of the urethra. The heating includes heating a portion of the vagina extending from the hymen inwardly to a location from 4.0 cm to 6.0 cm from the hymen.

In an embodiment of the invention, the method also involves heating at least part of a third portion of the subject's vagina, wherein the third portion is located on a posterior vaginal wall extending from about 3.0 cm to the left of a midline to about 3.0 cm to the right of the midline.

In an embodiment of the invention, any tissue residing outside of a first portion, a second portion or a third portion is not treated.

An embodiment of the invention relates to a method for treating urinary stress incontinence in a subject. The method includes the step of heating a subsurface region of a target tissue to a temperature between 45 degrees Celsius and 65 degrees Celsius.

An embodiment of the invention relates to a method for treating urinary stress incontinence in a subject. The method includes the step of heating a subsurface region of a target tissue to a temperature between 54 degrees C. and 60 degrees C.

An embodiment of the invention relates to a method for treating urinary stress incontinence in a subject. The method includes the step of heating a subsurface region of a target tissue by delivering of at least one of radiofrequency energy, microwave energy, laser energy, or ultrasound energy.

An embodiment of the invention relates to a method for treating urinary stress incontinence in a subject. The method includes the step of heating a subsurface region of a target tissue for a period of 1 second to 5 seconds.

An embodiment of the invention relates to a method for treating urinary stress incontinence in a subject. The method includes the step of heating a subsurface region of a target tissue for a period of time between 2 seconds and 4 seconds.

An embodiment of the invention relates to a method for treating urinary stress incontinence in a subject. The method includes the step of heating a subsurface region of a target tissue, the subsurface region being a submucosa tissue layer.

An embodiment of the invention relates to a method for treating urinary stress incontinence in a subject. The method includes the steps of heating a subsurface region of a target tissue and cooling a surface region of the target tissue. In some embodiments, the cooling of the surface region of the target tissue involves contacting an epithelial tissue layer of the target tissue with a treatment tip, the treatment tip including a cooling mechanism.

An embodiment of the invention relates to a method for treating urinary stress incontinence in a subject. The method includes the steps of heating a subsurface region of a target tissue and cooling a surface region of the target tissue. In some embodiments, the cooling of the surface region of the target tissue involves cooling the epithelial tissue layer to a temperature between 0 degrees C. and 10 degrees C.

An embodiment of the invention relates to a method for treating urinary stress incontinence in a subject. The method includes the steps of heating a subsurface region of a target tissue and cooling a surface region of the target tissue. In some embodiments, the cooling of the surface region of the target tissue precedes the heating, and continues during the heating.

An embodiment of the invention relates to a method for treating urinary stress incontinence in a subject. The method includes the steps of heating a subsurface region of a target tissue and cooling a surface region of the target tissue. In some embodiments, the cooling of the surface region of the target tissue is carried out during the heating, and continues after the heating.

An embodiment of the invention relates to a method for treating urinary stress incontinence in a subject. The method includes the steps of heating a subsurface region of a target tissue and contacting an epithelial tissue layer of the subject's vagina with a treatment tip at two or more contact sites during a procedure. The treatment tip includes an energy delivery element adapted to heat the target tissue. In some embodiments, the step of contacting an epithelial tissue layer of the subject's vagina with a treatment tip at two or more contact sites is repeated at least twice during the procedure such that each of the two or more contact sites is contacted at least twice.

An embodiment of the invention relates to a method for treating urinary stress incontinence in a subject. The method includes the step of heating a subsurface region of a target tissue to a predetermined temperature for a period of time sufficient to induce remodeling of the subsurface region. The remodeling includes at least one of contracting target tissue, denaturing collagen, tightening collagen-rich sites in the target tissue, or releasing heat shock proteins. In some embodiments, at least some of the remodeling occurs during the heating.

An embodiment of the invention relates to a method for treating urinary stress incontinence in a subject. The method includes the step of heating a subsurface region of a target tissue to a predetermined temperature for a period of time sufficient to induce remodeling of the subsurface region. The method also involves heating a subsurface region of a second target tissue to a predetermined temperature for a period of time sufficient to induce remodeling of the subsurface region of the second target tissue, wherein the second target tissue is a tissue around the subject's urethra and outside of the vaginal canal of the subject's vagina.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. The first period of time is shorter than the third period of time. The heating includes delivering energy by contacting an epithelial tissue layer in the subject's vagina with a treatment tip. The tip including an energy delivery element, and the heating includes heating a portion in the subject's vagina extending from the hymen inwardly to a location from 4.0 cm to 6.0 cm from the hymen.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. The heating of the subsurface region of the target tissue also includes the steps of: heating at least part of a first portion of the subject's vagina; and heating at least part of a second portion of the subject's vagina. The first portion is located on an anterior vaginal wall extending from about 0.25 cm to the left of the subject's urethra to about 2 cm to the left of the subject's urethra, and the second portion is located on the anterior vaginal wall extending from about 0.25 cm to the right of the urethra to about 2 cm to the right of the urethra. In some embodiments, the method includes the step of heating at least part of a third portion of the subject's vagina, wherein the third portion is located on a posterior vaginal wall extending from about 3.0 cm to the left of a midline to about 3.0 cm to the right of the midline. In some embodiments, any tissue residing outside of the first portion, the second portion or the third portion is not treated.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. Heating the target tissue includes heating the target tissue to a temperature between 45 degrees C. and 65 degrees C.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. Heating the target tissue includes heating the target tissue to a temperature between 54 degrees C. and 60 degrees C.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. Heating the target tissue involves delivering to the target tissue radiofrequency energy, microwave energy, laser energy, or ultrasound energy.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. The second period of time sufficient to induce remodeling of the target tissue is between 1 second and 5 seconds.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. The second period of time sufficient to induce remodeling of the target tissue is between 2 seconds and 4 seconds.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. The heating of the subsurface region of the target tissue includes heating a submucosa tissue layer, wherein the cooling of the surface region of the target tissue for a first period of time further includes cooling an epithelial tissue layer, and the cooling of the surface region of the target tissue for a third period of time further includes cooling the epithelial tissue layer.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. The cooling of the surface region of target tissue for a first period of time and the cooling of the surface region of the target tissue for a third period of time each include contacting an epithelial tissue layer with a treatment tip, the treatment tip including a cooling mechanism.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. The cooling of the surface region of the target tissue for a first period of time and the cooling of the surface region of the target tissue for a third period of time each include cooling the surface region of the target tissue to a temperature between 0 degrees C. and 10 degrees C.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. The cooling of the surface region of the target tissue is done during the heating of the subsurface region of the target tissue.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. The method also includes contacting an epithelial tissue layer of the subject's vagina with a treatment tip at two or more contact sites during a procedure. The treatment tip includes an energy delivery element adapted to heat the subsurface region of the target tissue. In some embodiments, the contacting of the epithelial tissue layer of the subject's vagina with a treatment tip at two or more contact sites is repeated at least twice during the procedure such that each of the two or more contact sites is contacted at least twice. In some embodiments, the contacting of the epithelial tissue layer of the subject's vagina with a treatment tip at two or more contact sites is repeated at least five times during the procedure such that each of the plurality of contact sites is contacted at least five times.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. The remodeling includes at least one of contracting target tissue, denaturing collagen, tightening collagen-rich sites in the target tissue, or releasing heat shock proteins.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. At least some of the remodeling occurs during the heating.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. In some embodiments the first period of time is at least 0.5 seconds. In some embodiments, the third period of time is at least 4 seconds.

An embodiment of the invention relates to a method for treating urinary stress incontinence in a subject. The method includes the steps of: cooling a surface region of a target tissue for a first period of time; heating a subsurface region of the target tissue to a predetermined temperature for a second period of time sufficient to induce remodeling of the target tissue; and cooling the surface region of the target tissue for a third period of time. The method also involves heating a subsurface region of a second target tissue to a predetermined temperature for a period of time sufficient to induce remodeling of the subsurface region of the second target tissue, wherein the second target tissue is a tissue around the subject's urethra and outside of the vaginal canal of the subject's vagina.

An embodiment of the invention relates to a method for treating urinary stress incontinence in a subject. The method includes the steps of: heating a subsurface region of a target tissue to a predetermined temperature for a period of time sufficient to induce remodeling of the subsurface region. The heating includes heating at least part of a first portion of the subject's vagina circumferentially around a wall of the subject's vagina from 10:30 to 1:30 while avoiding a portion directly above the subject's urethra, wherein an aspect closest to the subject's urethra is 12 o'clock, and wherein the heating includes heating a portion of the vagina extending from the hymen inwardly to a location from 4.0 cm to 6.0 cm from the hymen. In some embodiments, the method also includes heating at least part of a second portion of the subject's vagina circumferentially around a wall of subject's vagina from 5 o'clock to 7 o'clock, and wherein the second portion is diametrically opposed to the first portion. In some embodiments, any tissue residing outside of a first portion, a second portion or a third portion is not treated.

An embodiment of the invention relates to a method for treating urinary stress incontinence in a subject. The method includes the steps of: heating a subsurface region of a target tissue to a predetermined temperature for a period of time sufficient to induce remodeling of the subsurface region. The heating includes heating at least part of a first portion of the subject's vagina circumferentially around a wall of the subject's vagina from 10:30 to 1:30 while avoiding a portion directly above the subject's urethra, wherein an aspect closest to the subject's urethra is 12 o'clock, and wherein the heating includes heating a portion of the vagina extending from the hymen inwardly to a location from 4.0 cm to 6.0 cm from the hymen. In some embodiments, the method also includes heating the target tissue to a temperature between 45 degrees C. and 65 degrees C.

An embodiment of the invention relates to a method for treating urinary stress incontinence in a subject. The method includes the steps of: heating a subsurface region of a target tissue to a predetermined temperature for a period of time sufficient to induce remodeling of the subsurface region. The heating includes heating at least part of a first portion of the subject's vagina circumferentially around a wall of the subject's vagina from 10:30 to 1:30 while avoiding a portion directly above the subject's urethra, wherein an aspect closest to the subject's urethra is 12 o'clock, and wherein the heating includes heating a portion of the vagina extending from the hymen inwardly to a location from 4.0 cm to 6.0 cm from the hymen. In some embodiments, the method also includes heating the target tissue to a temperature between 54 degrees C. and 60 degrees C.

An embodiment of the invention relates to a method for treating urinary stress incontinence in a subject. The method includes the steps of: heating a subsurface region of a target tissue to a predetermined temperature for a period of time sufficient to induce remodeling of the subsurface region. The heating includes heating at least part of a first portion of the subject's vagina circumferentially around a wall of the subject's vagina from 10:30 to 1:30 while avoiding a portion directly above the subject's urethra, wherein an aspect closest to the subject's urethra is 12 o'clock, and wherein the heating includes heating a portion of the vagina extending from the hymen inwardly to a location from 4.0 cm to 6.0 cm from the hymen. In some embodiments, the method also includes delivering of at least one of radiofrequency energy, microwave energy, laser energy, or ultrasound energy.

An embodiment of the invention relates to a method for treating urinary stress incontinence in a subject. The method includes the steps of: heating a subsurface region of a target tissue to a predetermined temperature for a period of time sufficient to induce remodeling of the subsurface region. The heating includes heating at least part of a first portion of the subject's vagina circumferentially around a wall of the subject's vagina from 10:30 to 1:30 while avoiding a portion directly above the subject's urethra, wherein an aspect closest to the subject's urethra is 12 o'clock, and wherein the heating includes heating a portion of the vagina extending from the hymen inwardly to a location from 4.0 cm to 6.0 cm from the hymen. In some embodiments, the period of time sufficient to induce remodeling of the target tissue is between 1 second and 5 seconds.

An embodiment of the invention relates to a method for treating urinary stress incontinence in a subject. The method includes the steps of: heating a subsurface region of a target tissue to a predetermined temperature for a period of time sufficient to induce remodeling of the subsurface region. The heating includes heating at least part of a first portion of the subject's vagina circumferentially around a wall of the subject's vagina from 10:30 to 1:30 while avoiding a portion directly above the subject's urethra, wherein an aspect closest to the subject's urethra is 12 o'clock, and wherein the heating includes heating a portion of the vagina extending from the hymen inwardly to a location from 4.0 cm to 6.0 cm from the hymen. In some embodiments, the period of time sufficient to induce remodeling of the target tissue is between 2 seconds to 4 seconds.

An embodiment of the invention relates to a method for treating urinary stress incontinence in a subject. The method includes the steps of: heating a subsurface region of a target tissue to a predetermined temperature for a period of time sufficient to induce remodeling of the subsurface region. The heating includes heating at least part of a first portion of the subject's vagina circumferentially around a wall of the subject's vagina from 10:30 to 1:30 while avoiding a portion directly above the subject's urethra, wherein an aspect closest to the subject's urethra is 12 o'clock, and wherein the heating includes heating a portion of the vagina extending from the hymen inwardly to a location from 4.0 cm to 6.0 cm from the hymen. In some embodiments, the method also includes heating a submucosa tissue layer.

An embodiment of the invention relates to a method for treating urinary stress incontinence in a subject. The method includes the steps of: heating a subsurface region of a target tissue to a predetermined temperature for a period of time sufficient to induce remodeling of the subsurface region. The heating includes heating at least part of a first portion of the subject's vagina circumferentially around a wall of the subject's vagina from 10:30 to 1:30 while avoiding a portion directly above the subject's urethra, wherein an aspect closest to the subject's urethra is 12 o'clock, and wherein the heating includes heating a portion of the vagina extending from the hymen inwardly to a location from 4.0 cm to 6.0 cm from the hymen. In some embodiments, the method also includes cooling a surface region of the target tissue.

An embodiment of the invention relates to a method for treating urinary stress incontinence in a subject. The method includes the steps of: heating a subsurface region of a target tissue to a predetermined temperature for a period of time sufficient to induce remodeling of the subsurface region. The heating includes heating at least part of a first portion of the subject's vagina circumferentially around a wall of the subject's vagina from 10:30 to 1:30 while avoiding a portion directly above the subject's urethra, wherein an aspect closest to the subject's urethra is 12 o'clock, and wherein the heating includes heating a portion of the vagina extending from the hymen inwardly to a location from 4.0 cm to 6.0 cm from the hymen. In some embodiments, the method also includes cooling of the surface region of a target tissue by contacting an epithelial tissue layer of the target tissue with a treatment tip, the treatment tip including a cooling mechanism.

An embodiment of the invention relates to a method for treating urinary stress incontinence in a subject. The method includes the steps of: heating a subsurface region of a target tissue to a predetermined temperature for a period of time sufficient to induce remodeling of the subsurface region. The heating includes heating at least part of a first portion of the subject's vagina circumferentially around a wall of the subject's vagina from 10:30 to 1:30 while avoiding a portion directly above the subject's urethra, wherein an aspect closest to the subject's urethra is 12 o'clock, and wherein the heating includes heating a portion of the vagina extending from the hymen inwardly to a location from 4.0 cm to 6.0 cm from the hymen. In some embodiments, the method also includes cooling of the surface region of a target tissue by contacting an epithelial tissue layer of the target tissue with a treatment tip, the treatment tip including a cooling mechanism. In some embodiments, the method also includes cooling the epithelial tissue layer to a temperature between 0 degrees C. and 10 degrees C.

An embodiment of the invention relates to a method for treating urinary stress incontinence in a subject. The method includes the steps of: heating a subsurface region of a target tissue to a predetermined temperature for a period of time sufficient to induce remodeling of the subsurface region. The heating includes heating at least part of a first portion of the subject's vagina circumferentially around a wall of the subject's vagina from 10:30 to 1:30 while avoiding a portion directly above the subject's urethra, wherein an aspect closest to the subject's urethra is 12 o'clock, and wherein the heating includes heating a portion of the vagina extending from the hymen inwardly to a location from 4.0 cm to 6.0 cm from the hymen. In some embodiments, the method also includes cooling of the surface region of a target tissue by contacting an epithelial tissue layer of the target tissue with a treatment tip, the treatment tip including a cooling mechanism. In some embodiments, the cooling precedes the heating, and continues during the heating.

An embodiment of the invention relates to a method for treating urinary stress incontinence in a subject. The method includes the steps of: heating a subsurface region of a target tissue to a predetermined temperature for a period of time sufficient to induce remodeling of the subsurface region. The heating includes heating at least part of a first portion of the subject's vagina circumferentially around a wall of the subject's vagina from 10:30 to 1:30 while avoiding a portion directly above the subject's urethra, wherein an aspect closest to the subject's urethra is 12 o'clock, and wherein the heating includes heating a portion of the vagina extending from the hymen inwardly to a location from 4.0 cm to 6.0 cm from the hymen. In some embodiments, the method also includes cooling of the surface region of a target tissue by contacting an epithelial tissue layer of the target tissue with a treatment tip, the treatment tip including a cooling mechanism. In some embodiments, the cooling is carried out during the heating, and continues after the heating.

An embodiment of the invention relates to a method for treating urinary stress incontinence in a subject. The method includes the steps of: heating a subsurface region of a target tissue to a predetermined temperature for a period of time sufficient to induce remodeling of the subsurface region. The heating includes heating at least part of a first portion of the subject's vagina circumferentially around a wall of the subject's vagina from 10:30 to 1:30 while avoiding a portion directly above the subject's urethra, wherein an aspect closest to the subject's urethra is 12 o'clock, and wherein the heating includes heating a portion of the vagina extending from the hymen inwardly to a location from 4.0 cm to 6.0 cm from the hymen. Some embodiments include heating a subsurface region of a second target tissue to a predetermined temperature for a period of time sufficient to induce remodeling of the subsurface region of the second target tissue, wherein the second target tissue is a tissue around the subject's urethra and outside the vaginal canal of the subject's vagina.

The method and apparatus, as provided by embodiments of the invention, are non-invasive and substantially non ablative of vaginal issue. The nature of the engagement between the apparatus and vaginal tissue is that of contacting a treatment tip to an epithelial surface of the vaginal tissue. Through such contact, the apparatus delivers heat to underlying tissue, while preventing the heating of the surface epithelium by cooling it.

In a particular embodiment, the invention provides a method and apparatus for treating urinary stress incontinence through the use of radiofrequency (RF) energy delivered through the vaginal epithelial tissue and to the respective underlying layers that are the target tissue of embodiments of the invention. Other embodiments may make use of other forms of energy, such as microwave, laser, or ultrasound.

In an embodiment of the invention, RF energy is delivered to target tissue with a cooling source. In such an embodiment, cooling before an RF pulse sequence begins initially protects the mucosal surface from thermal damage while the RF energy passes through it. RF energy drives deep into the tissue generating heat with the goal of provoking a cytokine cascade including various heat shock proteins, optimally even denaturing collagen and provoking neo-collagenesis. Cooling after the RF pulse sequence ends quenches the heat in the treated tissue, preventing heat buildup as the adjacent area is treated. In other embodiments, cooling before the RF pulse sequence draws out heat from the mucosa by the bulk-cooling effect, also with the goal of provoking a cytokine and heat shock protein cascade. Quenching the bulk cooling with the application of RF energy quickly returns the tissue to normal temperature, preserving its viability and preventing cold induced necrosis. The RF energy may be delivered by a monopolar RF energy source or a bipolar RF energy source. In some embodiments, a monopolar energy source is preferred.

In an embodiment of the invention, RF energy is delivered to target tissue alone and without the application of a secondary energy or cooling source. In such an embodiment, RF energy drives deep into the tissue generating heat with the goal of provoking a cytokine cascade including various heat shock proteins, optimally even denaturing collagen and provoking neo-collagenesis.

In an embodiment of the invention, ultrasound energy is delivered to target tissue. In such an embodiment, ultrasound energy as applied by a delivery system exceeds the collagen denaturation threshold far more quickly with the effect of causing a lesion that provokes a certain amount of tissue turnover in a somewhat randomized, fractionated pattern. The benefit of a fractionated approach is that the small lesions, or islands of damaged tissue can be repaired with the help of the healthy tissue surrounding them. This has been shown to speed healing and tissue turnover in other fractional techniques, such as those involving lasers.

In an embodiment of the invention, a laser is used to heat target tissue. For example, energy from an ErbiumYAG laser at 2,940 nm can be delivered to a target tissue. Rapid vaporization of target surface tissue is achieved, optimally in a fractionated pattern. This is done without the ability to penetrate beyond a depth of 25-30 microns per 1 ms pulse or to deposit significant enough heat to denature collagen surrounding the vaporization hole. Multiple single millisecond pulses making up a longer pulse sequence can be used. The primary benefit would be tissue turnover.

In another embodiment, a $CO_2$ Laser at 10,600 nm can be used to achieve somewhat less rapid vaporization of target tissue, optimally in a fractionated pattern, with the ability to penetrate to a depth of 50-100 microns per 1 ms pulse and the deposition of up to 150 microns of residual heat necrosis per pulse. This residual heat provides homeostasis and provokes a robust cytokine/heat shock protein response.

Multiple single ms pulses making up a longer pulse sequence are common. The primary benefits of tissue turnover and heat shock protein cascade improve vaginal atrophy and vaginal dryness syndrome.

In an embodiment of the invention, energy from a laser is applied to target tissue with cooling. In such an embodiment, a laser is coupled with a cryogen based cooling mechanism to protect the skin. The combination is often employed during high fluence, non-ablative laser hair removal treatments and other treatments where a heat based interaction with the target chromophore is required (ie. vascular and pigmented lesion treatments). It is also used to selectively protect a non-target chromophore with similar absorption characteristics as the intended target by pre-cooling it to survive the heat rise from a pulse intended for a deeper target.

In some embodiments, RF is the preferred energy source over laser or ultrasound. Laser energy can rapidly raise the temperature of the surface layer of tissue, but might not be able to raise the temperature of subsurface tissue layers as effectively and efficiently as RF. In addition, prolonged application of laser energy to a target tissue might cause undesired damage to the surface layer of the tissue, especially if one is applying laser energy with the intent of raising the temperature of subsurface tissue. Although ultrasound might be more effective at heating subsurface tissue layers than RF, it might also cause greater discomfort to the subject leading to premature termination of therapy sessions. As a result, RF is the preferred energy source over ultrasound in some embodiments.

Some embodiments of the invention provide a method and apparatus for creating a reverse thermal gradient that utilizes one or more RF electrodes to convey energy that manifests as heat in the target tissue, and a mechanism to cool the epithelial surface above the targeted underlying layers. A purpose of cooling the epithelial surface is to protect it from potentially damaging effects of excess heat that would accumulate in the absence of cooling. The epithelial surface is thus a conduit for energy passing through to underlying layers, but the energy does not manifest in the form of increased temperature at the epithelial surface. As such, the epithelium itself is not damaged or substantially modified by the method. Such protection from heating may derive both from the heat-sink aspect of a cooled body, as well as an increase in tissue impedance that is associated with cooled tissue.

In some embodiments, the cooling mechanism of the apparatus includes a lumen adapted to accommodate a cooling fluid conveyed to nozzles, which cool the energy delivery element of treatment tip of the apparatus. Embodiments of the method thus provide for contacting a contact site on a genital epithelial surface, the tip having the capability both to cool the surface epithelium and to heat the underlying tissue. The cooling fluid cools the treatment tip of the apparatus, as provided by embodiments of the invention; in turn, the surface of the cooled treatment tip cools the surface of the mucosal epithelium that the treatment tip contacts. As provided by embodiments of the invention, the epithelial surface may be cooled to a temperature range of about 0 degrees C. to about 10 degrees C. As energy from the tip passes through the mucosal epithelial surface, the underlying soft tissue may be heated to a temperature range of about 45 degrees C. to about 65 degrees C. Thus, a reverse thermal gradient is created, with a lower temperature at the mucosal epithelium, and a higher temperature in the underlying tissue.

Some embodiments of the method include heating the target zone using a radiant energy source, typically an RF energy source, but other embodiments may use microwave, ultrasound energy, laser, or magnetic potential energy sources. Some embodiments include contacting the mucosal epithelium with a treatment tip that has an energy delivering element and a cooling mechanism. By delivering energy to the tissue while cooling the epithelial surface, a reverse thermal gradient is created. The RF energy penetrates through the cooled epithelium and into the underlying target tissue, and heats the tissue.

In typical embodiments of the invention, the method provides for surface cooling coincident with the time that heat is being delivered to underlying tissue. In some embodiments, in addition to cooling the surface while heating the underlying tissue, the method includes a period of cooling before the application of heat. In other embodiments, the method includes a period of cooling after the application of heat. In still other embodiments, the method includes cooling both before and after the application of heat.

A procedure, such as would take place in a visit to a medical office, would typically include contacting the epithelium within the vagina and applying a sequence of pulses. During the same procedure, the treatment tip may be returned to the same contact point multiple times. The total treatment time may be about 30 minutes.

The method according to some embodiments comprises remodeling of the target tissue. The application of energy to the underlying connective tissue creates heat in the targeted tissue, and the heat is understood to have an immediate or nearly immediate effect of denaturing or partially-denaturing collagen in the tissue, this denaturation of collagen being a factor in the tissue remodeling. In other embodiments of the invention, the application of heat to the connective tissue during a treatment procedure is understood to result in a subsequent depositing of new or nascent collagen by cells of the connective tissue, as part of a biological process that may take place over the course of weeks or months following the procedure. The heat can also induce expression of heat shock proteins and initiation of heat shock protein cascades.

As provided by embodiments of the invention, remodeling of vaginal tissue, whether by denaturation of collagen in the tissue, or by subsequent deposition of new collagen in the tissue, results in a tightening of vaginal tissue. A consequence of the heating of the target tissue may include a melting or denaturing of preexisting collagen in the tissue, which may reduce or compact the volume occupied by the collagen, the effect of which is to tighten surrounding tissue. A longer term biological consequence of the heating may include a healing process in which there is an increase in the rate of cellular production and deposition into the extracellular space. Both types of responses, the near-immediate response of pre-existing collagen, and the longer term increased amount of collagen are understood to contribute to an overall tightening of the target tissue, which can result in reduction or even elimination of urinary stress incontinence.

The overall length of the treatment tip, from the base of the connector portion to the foremost point of the distal portion is designed such that the side mounted energy delivery element reaches the innermost region of the vagina that is treated by the tip. Accordingly, embodiments of the tip may have an overall length of between about 2.75 inches and 4.25 inches. Particular embodiments have an overall length of between about 3 inches and about 4 inches. Still more embodiments have an overall length of between about 3.25 inches and about 3.75 inches. This overall length is appropriate for providing the treatment tip access to the portion of a gently unfolded vagina proximal to the hymen.

An energy delivery element is positioned on an end of the treatment tip. The energy delivery element can have dimensions adapted to making approximately flat contact with the vaginal wall. The width of the element, an RF electrode in typical embodiments, in some embodiments is between about 0.7 cm and about 1.3 cm. In other embodiments, the width is between about 0.8 cm and about 1.2 cm. In still other embodiments, the width is between about 0.9 cm and about 1.1 cm. In some embodiments, the length of the energy delivery element is between about 2 and about 6 cm. In other embodiments, the length is between about 2.25 cm and about 2.75 cm. The method of treatment typically comprises treating the vagina at a point no deeper than about 6 cm in from the hymen. The width of the energy delivery element can enable the element to make a substantially flat contact with the inner aspect of a curved surface. In some embodiments the width can be 2 cm or 1 cm. By constraining the width of the contact site, an increased pressure or closeness of contact that could occur along lengthwise edges is minimized.

According to some embodiments of the invention, the energy delivery element has a flat configuration. In other embodiments the energy delivery element comprises a curved surface such that it includes a curvature radially with respect to the linear axis while remaining parallel to the linear axis, the form representing an arc of a cylinder. The arc of the curvature may be as large as approximately 30 degrees. Some embodiments may include a curvature of about 30 degrees. This 30 degrees of curvature is adapted to fit the curvature of the vaginal wall. The surface area of the energy delivery element that contacts the tissue can be between 2 cm$^2$ to 12 cm$^2$.

The energy delivery element may be any of an RF electrode, a microwave emitter, a laser, or an ultrasound emitter. The RF electrode, in some embodiments, is a capacitive electrode, which capacitively couples to the mucosal epithelium. The RF electrode, without limiting the scope of the invention, may have a thickness in the range of about 0.01 to about 1.0 mm.

Additionally, the electrode may be equipped with an integrated EEROM (Electrically Erasable Read Only Memory, also known as EEPROM) programmable memory chip at any suitable location within the treatment tip (not shown). Such a chip may provide identifying information or other information about the operational status or configuration parameters of the RF electrode to the system, such parameters may include, by way of example, the type and size of the electrode, the number of times the energy delivery element has been fired, and the like. Additionally, thermisters (thermal sensors) may be provided at each corner of an RF electrode, or otherwise in close proximity to the electrode, to provide feedback to the system on the temperature at their location.

In some embodiments, the treatment tip as a whole is designed as a single-use disposable component, while the hand piece is typically a reusable instrument. The single-use and disposable aspects of treatment tip are in accord with its designated use in a single procedure, in the context of a female patient having a procedure, per embodiments of the method further described below, in a medical setting.

The apparatus is included in a larger electronic system (not shown) with features known in the art. Embodiments comprise a power source, an RF power source in typical embodiments that feeds energy to an RF power generator and power flows therefrom to RF electrodes. RF waves produced range from 3 kHz to 300 GHz. A multiplexer measures current, voltage and temperature, at the thermal sensors associated with to each RF electrode. The multiplexer is driven by a controller, which can be a digital or analog controller, or a computer with software. The controller may turn the energy source and cooling source, if the treatment apparatus includes a cooling source, on and off. The controller may determine the length of each heating and/or cooling period in a given "pulse." The controller may provide multiple different types of pulses that may vary in the duration of heating or cooling. The controller may provide an indication that a pulse has ended, for example, by providing a visual or audio queue. When the controller is a computer it can include a CPU coupled through a system bus. On the system there may also be a keyboard, disk drive, or other non-volatile memory systems, a display, and other peripherals, as are well known in the art. Also coupled to the bus may be a program memory and a data memory.

An operator interface includes operator controls and a display. The controller can be coupled to different types of imaging systems including ultrasonic, thermal sensors, and impedance monitors. Current and voltage are used to calculate impedance. A diagnostic phase can be initially run to determine the level of treatment activity. This can be done through ultrasound as well as other means. Diagnostics can be performed both before and after treatment.

Other variations of treatment tip design and associated methods can be employed to achieve the objectives of the invention without departing from the scope of the invention, as will be appreciated by those skilled in the art. The shape and dimensions of the tip can also be adjusted, as desired, to enhance the effectiveness of the treatment taking into consideration physiological and anatomical information. While various embodiments of the present invention have been shown and described herein, it will be obvious to those skilled in the art that such embodiments are provided by way of example only. Although the description has offered the theory that collagen denaturation underlies the remodeling of tissue brought about by practicing the invention, and theory has also been offered that tissue remodeling may occur as a result of the deposition of collagen by connective tissue at a time after the inventive procedure has been performed. Some theory has also been offered to explain the nature of the protection afforded to the mucosal epithelium by cooling it. Such theories have been offered simply as possible theories of how the invention works and as an aid in describing the invention, however, it should be understood that such theories and interpretation do not bind or limit the claims with regard to tissue remodeling brought about by the practice of the invention. Numerous variations, changes, and substitutions will now occur to those skilled in the art without departing from the invention. It should be understood that various alternatives to the embodiments of the invention described herein may be employed in practicing the invention. It is intended that the scope of the invention, methods and structures within the scope of the invention includes equivalents.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method for treating urinary stress incontinence in a subject, the method comprising:
   non-invasively treating a subsurface region of a target tissue to a temperature for a period of time sufficient to induce a remodeling of the subsurface region; and
   inducing remodeling of the subsurface region to treat urinary stress incontinence,
   wherein the step of non-invasively treating comprises:
      treating at least part of a first portion of a vagina of the subject, the first portion located on an anterior vaginal wall to a left of a urethra of the subject;
      treating at least part of a second portion of the vagina, the second portion located on the anterior vaginal wall to a right of the urethra; and
      treating at least part of a third portion of the vagina, wherein the third portion is located on a posterior vaginal wall extending along a midline,
   wherein the first, second and third portions are separated from each other by portions of the vagina that remain untreated whereby the untreated portions reside outside of the first portion, the second portion or the third portion, and
   wherein the untreated portions comprise a first untreated portion located on a lateral wall of the vagina between the first portion located on the anterior vaginal wall to the left of the urethra and the third portion located on the posterior vaginal wall, and a second untreated portion located on a lateral wall of the vagina between the second portion located on the anterior vaginal wall to the right of the urethra and the third portion located on a posterior vaginal wall.

2. The method according to claim 1, wherein the step of inducing remodeling of the subsurface region further comprises inducing positioning of a urethra to treat urinary stress incontinence.

3. The method according to claim 1, wherein the step of non-invasively treating further comprises heating to at least one of a predetermined temperature for a predetermined period of time to induce remodeling of the subsurface region to treat urinary incontinence.

4. The method according to claim 1, wherein the step of non-invasively treating further comprises treating the anterior vaginal wall proximate and apart from the urethra of the subject, and avoiding directly treating the urethra to the temperature, and inducing remodeling of the subsurface region to create a buttress of remodeled tissue to support the urethra to treat urinary stress incontinence.

5. The method according to claim 1, wherein the step of non-invasively treating further comprises treating the posterior vaginal wall, inducing remodeling of the subsurface region of the posterior vaginal wall to treat urinary stress incontinence by the remodeled posterior vaginal wall providing a buttress of remodeled tissue to support the anterior vaginal wall when compressed against the posterior vaginal wall.

6. The method according to claim 1, further comprising the step of cooling the target tissue.

7. The method according to claim 1, wherein the step of non-invasively treating comprises: heating at least part of the first portion of the vagina of the subject, the first portion located on the anterior vaginal wall extending from about 0.25 cm to a left of the urethra of the subject to about 2 cm to the left of the urethra; and heating at least part of the second portion of the vagina, the second portion located on the anterior vaginal wall extending from about 0.25 cm to a right of the urethra to about 2 cm to the right of the urethra, wherein the heating includes heating a portion of the vagina extending from a hymen inwardly to a location from 4.0 cm to 6.0 cm from the hymen.

8. The method according to claim 7, wherein the step of non-invasively treating the subsurface region of the target tissue further comprises heating at least part of the third portion of the vagina, wherein the third portion is located on the posterior vaginal wall extending from about 3.0 cm to a left of the midline to about 3.0 cm to a right of the midline.

9. The method according to claim 8, wherein any tissue residing outside of the first portion, the second portion or the third portion is not treated.

10. The method according to claim 1, wherein the step of non-invasively treating comprises heating the target tissue to a temperature between 45 degrees C. and 65 degrees C.

11. The method according to claim 1, wherein the step of non-invasively treating comprises heating the target tissue to a temperature between 54 degrees C. and 60 degrees C.

12. The method according to claim 1, wherein the step of non-invasively treating further comprises delivering of at least one of radiofrequency energy, microwave energy, laser energy, or ultrasound energy.

13. The method according to claim 1, wherein the period of time sufficient to induce remodeling of the subsurface region is between 1 second to 5 seconds.

14. The method according to claim 1, wherein the period of time sufficient to induce remodeling of the subsurface region is between 2 seconds to 4 seconds.

15. The method according to claim 1, wherein the step of non-invasively treating further comprises heating a submucosa tissue layer.

16. The method according to claim 1, further comprising cooling a surface region of the target tissue.

17. The method according to claim 16, wherein the cooling the surface region of the target tissue comprises contacting an epithelial tissue layer of the target tissue with a treatment tip, the treatment tip including a cooling mechanism.

18. The method according to claim 17, wherein the cooling the surface region comprises cooling the epithelial tissue layer to a temperature between 0 degrees C. and 10 degrees C.

19. The method according to claim 1, further comprising contacting an epithelial tissue layer of the vagina of the subject with a treatment tip at two or more contact sites during a procedure, wherein the treatment tip comprises an energy delivery element adapted to non-invasively treat the target tissue.

20. The method according to claim 19, wherein the step of contacting the epithelial tissue layer of the vagina with a treatment tip at two or more contact sites is repeated at least twice during the procedure such that each of the two or more contact sites is contacted at least twice.

21. The method according to claim 19, wherein the step of contacting the epithelial tissue layer of the vagina with a treatment tip at two or more contact sites is repeated at least five times during the procedure such that each of the two or more contact sites is contacted at least five times.

22. The method according to claim 1, wherein the remodeling comprises at least one of contracting the target tissue, denaturing collagen, tightening collagen-rich sites in the target tissue, or releasing heat shock proteins.

23. The method according to claim 1, wherein at least some of the remodeling occurs during the step of non-invasively treating.

24. The method according to claim 1, further comprising: cooling a surface region of the target tissue for a first period of time; and cooling the surface region of the target tissue for a second period of time, wherein the first period of time is shorter than the second period of time, wherein the step of non-invasively treating comprises delivering energy by contacting an epithelial tissue layer in the vagina of the subject with a treatment tip, the treatment tip including an energy delivery element, and wherein the step of non-invasively treating includes heating a portion in the vagina extending from a hymen inwardly to a location from 4.0 cm to 6.0 cm from the hymen.

25. The method according to claim 24, wherein the step of non-invasively treating further comprises heating a submucosa tissue layer, wherein the step of cooling the surface region of the target tissue for the first period of time further comprises cooling an epithelial tissue layer, and wherein the step of cooling the surface region of the target tissue for the second period of time further comprises cooling the epithelial tissue layer.

26. The method according to claim 25, wherein the step of cooling the surface region of the target tissue for the first period of time and the step of cooling the surface region of the target tissue for the second period of time each further comprise contacting an epithelial tissue layer with the treatment tip, the treatment tip including a cooling mechanism.

27. The method according to claim 25, wherein the step of cooling the surface region of the target tissue for the first period of time and the step of cooling the surface region of the target tissue for the second period of time each further comprise cooling the surface region of the target tissue to a temperature between 0 degrees C. and 10 degrees C.

28. The method according to claim 1, wherein the step of non-invasively treating comprises treating at least part of the first portion of the vagina of the subject circumferentially around a wall of the vagina from 11 o'clock to 1 o'clock, wherein an aspect closest to the urethra of the subject is 12 o'clock.

29. The method according to claim 28, wherein the step of non-invasively treating further comprises treating at least part of the second portion of the subject's vagina circumferentially around a wall of the subject's vagina between 5 o'clock to 7 o'clock, and wherein the second portion is diametrically opposed to the first portion.

30. The method according to claim 29, wherein any tissue residing outside of the first portion or the second portion is not treated.

31. The method according to claim 28, wherein the step of non-invasively treating comprises one of: heating the target tissue to a temperature between 45 degrees C. and 65 degrees C.; and heating the target tissue to a temperature between 54 degrees C. and 60 degrees C.

32. The method according to claim 28, wherein the period of time sufficient to induce remodeling of the target tissue is one of: between 1 second to 5 seconds and between 2 seconds to 4 seconds.

33. The method according to claim 28, further comprising cooling a surface region of the target tissue, wherein the cooling the surface region of the target tissue comprises contacting an epithelial tissue layer of the target tissue with a treatment tip, the treatment tip including a cooling mechanism.

34. The method according to claim 33, wherein the cooling the surface region of the target tissue comprises cooling the epithelial tissue layer to a temperature between 0 degrees C. and 10 degrees C.

35. The method according to claim 28, wherein the step of non-invasively treating further comprises at least one of treating at least part of the second portion of the vagina circumferentially around a wall of the vagina between 1 o'clock to 5 o'clock and treating at least part of the second portion of the vagina circumferentially around a wall of the vagina between 7 o'clock to 11 o'clock.

36. The method according to claim 1, wherein the step of non-invasively treating is non-ablative.

37. The method according to claim 1, wherein the step of non-invasively treating comprises non-invasively heating the subsurface region of the target tissue to the temperature for the period of time sufficient to induce the remodeling of the subsurface region.

38. The method according to claim 1, wherein the step of non-invasively treating the subsurface region of the target tissue comprises cooling the target tissue.

* * * * *